(12) United States Patent
Shim et al.

(10) Patent No.: US 10,434,195 B2
(45) Date of Patent: Oct. 8, 2019

(54) METHYLSULFONAMIDE DERIVATIVES AND USES RELATED THERETO

(71) Applicant: Emory University, Atlanta, GA (US)

(72) Inventors: Hyunsuk Shim, Atlanta, GA (US);
Mark M. Goodman, Atlanta, GA (US);
Dinesh Shetty, Atlanta, GA (US);
Hyeun Yoon Oum, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/750,086

(22) PCT Filed: Aug. 3, 2016

(86) PCT No.: PCT/US2016/045288
§ 371 (c)(1),
(2) Date: Feb. 2, 2018

(87) PCT Pub. No.: WO2017/023999
PCT Pub. Date: Feb. 9, 2017

(65) Prior Publication Data
US 2018/0228924 A1    Aug. 16, 2018

Related U.S. Application Data

(60) Provisional application No. 62/200,319, filed on Aug. 3, 2015.

(51) Int. Cl.
| A61K 51/00 | (2006.01) |
| A61M 36/14 | (2006.01) |
| A61K 51/04 | (2006.01) |
| A61K 31/5377 | (2006.01) |
| A61K 45/06 | (2006.01) |
| C07B 59/00 | (2006.01) |
| C07D 249/06 | (2006.01) |

(52) U.S. Cl.
CPC ...... *A61K 51/0463* (2013.01); *A61K 31/5377* (2013.01); *A61K 45/06* (2013.01); *A61K 51/0453* (2013.01); *A61K 51/0459* (2013.01); *C07B 59/002* (2013.01); *C07D 249/06* (2013.01); *C07B 2200/05* (2013.01)

(58) Field of Classification Search
CPC .............. C07B 2200/05; C07B 59/002; A61K 51/0463; A61K 51/0459
USPC ....................................................... 424/1.89
See application file for complete search history.

(56) References Cited

U.S. PATENT DOCUMENTS

| 9,023,318 | B2 | 5/2015 | Chen |
| 2006/0009467 | A1 | 1/2006 | Josien |
| 2007/0258893 | A1 | 11/2007 | Shim |
| 2009/0099194 | A1* | 4/2009 | Liotta ............... C07D 239/42 514/252.14 |
| 2012/0294803 | A1* | 11/2012 | Shim ............... A61K 31/505 424/1.89 |
| 2013/0217887 | A1 | 8/2013 | Chen |
| 2015/0157630 | A1 | 6/2015 | Wilson |

FOREIGN PATENT DOCUMENTS

| WO | 2005/042489 | 5/2005 | |
| WO | 2006/067376 A2 | 6/2006 | |
| WO | WO-2006067376 A2 * | 6/2006 | .......... A61K 51/088 |
| WO | 2008/109154 A1 | 9/2008 | |

OTHER PUBLICATIONS

Mooring et al. ChemMedChem 2013, 8, 622-632.*
Sirion et al. Tetrahedron Lett. 48 (2007) 3953-3957.*
Bressler, et al. Preventative ophthalmology. Age-related macular degeneration. Ophthalmology. 1995, 102 (8):1206-1211.
CAS Registry No. 1394738-93-2 Sep. 18, 2012.
CAS Registry No. 1646745-83-6 Feb. 12, 2015.
Crane et al., CXCR4 Receptor Expression on Human retinal Pigment Epithelial Cells from the Blood-Retina Barrier Leads to Chemokine Secretion and Migration in Response to Stromal Cell-Derived Factor 1α, J. Immunol. 2000, 165:4372-4278.
Debnath et al. Small Molecule Inhibitors of CXCR4, 2013, 3(1):47-75.
Dwinell et al. Chemokine receptor expression by human intestinal epithelial cells, Gastroenterology. 1999, 117:359-367.
Goodman et al., Synthesis and characterization of iodine-123 labeled 2beta-carbomethoxy-3beta-(4'-((Z)-2-iodoethenyl)phenyl) nortropane. J Med Chem, 2003, 46(6):925-35.
Gupta et. al. Chemokine Receptors in Human Endothelial Cells. The Journal of Biological Chemistry, 1998, 273 (7):4282-4287.
Hanaoka et al. Development of a 111In-labeled peptide derivative targeting a chemokine receptor, CXCR4, for imaging tumors, Nuclear Medicine and Biology 33 (2006) 489-494.
Jacobson et al., 2009, 64Cu-AMD3100—A novel imaging agent for targeting chemokine receptor CXCR4, Bioorganic & Medicinal Chemistry 17: 1486-1493.
Jewett, A Simple Synthesis of [11C]Methyl Triflate Appl. Radiat. Isot. 2012, 43: 1383-1385.
Li et al., Synthesis of structurally identical fluorine-18 and iodine isotope labeling compounds for comparative imaging. Bioconjug Chem, 2003, 14(2):287-94.
Liang et al., Development of a Unique Small Molecule Modulator of CXCR4, PLoS ONE 7(4): e34038.
Maziere et al., 76Br-beta-CBT, a PET tracer for investigating dopamine neuronal uptake. Nucl Med Biol, 1995, 22 (8):993-7.
Misra et al. Quantitation of CXCR4 Expression in Myocardial Infarction Using 99mTc-Labeled SDF-1alpa, J Nucl Med 2008; 49:963-969.

(Continued)

Primary Examiner — Michael G. Hartley
Assistant Examiner — Sean R Donohue
(74) Attorney, Agent, or Firm — Emory Patent Group

(57) ABSTRACT

This disclosure relates to methylsulfonamide derivatives and uses as imaging agents and other uses related to CXCR4 inhibition. In certain embodiments, the disclosure relates to pharmaceutical compositions comprising compounds disclosed herein, derivatives, or pharmaceutically acceptable salts or prodrugs thereof. In certain embodiments, the compositions disclosed herein are used for imaging to study CXCR4 related conditions.

20 Claims, 16 Drawing Sheets

(56) References Cited

OTHER PUBLICATIONS

Mooring et al. Benzenesulfonamides: A Unique Class of Chemokine Receptor Type 4 Inhibitors, ChemMedChem. 2013, 8(4):622-32.

Murdoch et al. Functional expression of chemokine receptor CXCR4 on human epithelial cells, Immunology 1999 98 36-41.

Nimmagadda et al. Molecular Imaging of CXCR4 Receptor Expression in Human Cancer Xenografts with [64Cu] AMD3100 Positron Emission Tomography, Cancer Res. 2010, 70(10):3935-44.

Nishizawa et al. Fluorescent imaging of high-grade bladder cancer using a specific antagonist for chemokine receptor CXCR4, Int. J. Cancer: 127, 1180-1187 (2010).

Nomura et al. Fluorophore Labeling Enables Imaging and Evaluation of Specific CXCR4-Ligand Interaction at the Cell Membrane for Fluorescence-Based Screening, Bioconjugate Chem. 2008, 19, 1917-1920.

Plisson et al, Synthesis, radiosynthesis, and biological evaluation of carbon-11 and iodine-123 labeled 2beta-carbomethoxy-3beta[4'-((Z)-2-haloethenyl)phenyl]tropanes. J Med Chem, 2004, 47(5):1122-35.

Plisson et al, Synthesis, Radiosynthesis, and Biological Evaluation of Fluorine-18 Labeled 2β-Carb (fluoroalkoxy)-3β-(3'-((Z)-2-haloethenyl)phenyl)nortropanes: Candidate Radio ligands for In Vivo Imaging of the Serotonin Transporter with Positron Emission Tomography, J Med Chem. 2008,51(24): 7788-7799.

Shetty et al. Development of F-18 labeled inflammation-reporting PET tracer using click chemistry, J Nucl Med. 2013 vol. 54 No. supplement 2 59.

Sirion et al. An efficient F-18 labeling method for PET study: Huisgen 1,3-dipolar cycloaddition of bioactive substances and F-18-labeled compounds, Tetrahedron Letters 48 (2007) 3953-3957.

Villemagne et al. PET imaging of human cardiac opioid receptors, Eur J Nucl Med (2002) 29:1385-1388.

Volin, et. al. Chemokine Receptor CXCR4 Expression in Endothelium. Biochemical and Biophysical Research Communications 1998, 242:46-53.

Watkins et al. A Captive Solvent Method for Rapid N-[11C]Methylation of Secondary Amides: Application to the Benzodiazepine, 4'-Chlorodiazepam (R05-4864), Appl Radiat Isot. vol. 39, No. 5, pp. 441-444, 1988.

Wester et al. Disclosing the CXCR4 Expression in Lymphoproliferative Diseases by Targeted Molecular Imaging, Theranostics, 2015; 5(6): 618-630.

Wilson et al. In Viwo Evaluation of [11C]- and [ 18F]Labelled Cocaine Analogues as Potential Dopamine Transporter Ligands for Positron Emission Tomography, Nuclear Medicine & Biology, vol. 23, pp. 141-146, 1996.

Zhu et al. Development of F-18 labeled CXCR4 PET tracer, J Nucl Med May 2010 vol. 51 No. supplement 2 1532.

\* cited by examiner

METHYLSULFONAMIDE DERIVATIVES AND USES RELATED THERETO

CROSS-REFERENCE TO RELATED APPLICATIONS

This application is the National Stage of International Application No. PCT/US2016/045288 filed Aug. 3, 2016, which claims the benefit of priority to U.S. Provisional Application No. 62/200,319 filed Aug. 3, 2015. The entirety of each of these applications is hereby incorporated by reference for all purposes.

STATEMENT REGARDING FEDERALLY FUNDED RESEARCH

This invention was made with government support under Grants P50CA128301 and R01CA165306 awarded by the National Institutes of Health. The government has certain rights in the invention.

BACKGROUND

The chemokine stromal-derived factor-1alpha (SDF-1alpha, CXCL12) and its receptor CXCR4 are implicated in cancer metastasis and inflammation. Weiss & Jacobson, Bioorg Med Chem, 2009, 17(4): 1486-93 and Misra et al, Nucl Med, 2008, 49(6):963-9. Plerixafor (AMD3100) is a known CXCR4 antagonist that has been approved for the mobilization of hematopoietic stem cells by the U.S. Food and Drug Administration. Jacobsen et al. report labeling AMD3100 with the radioisotope $^{64}$Cu. Bioorg Med Chem, 2009, 17(4): 1486-93. Biodistribution of $^{64}$Cu-AMD3100 showed accumulation in CXCR4-expressing organs. U.S. Patent Application Publication Numbers 2007/0258893 and 2012/0294803 describe imaging compositions and methods for detection of biological conditions associated with expression of CXCR4 receptors. Other imaging agents that target CXCR4 have been reported. See Nimmagadda et al, Cancer research, 2010, 70(10):3935-44; Liang et al, PLoS ONE, 2012, 7(4):e34038; Hanaoka et al, Nucl Med Biol, 2006, 33(4):489-94; Nishizawa et al, Inter J Cancer, 2010, 127(5):1180-7; Nomura et al, Bioconjug Chem, 2008, 19(9): 1917-20. One of the noteworthy peptidic CXCR4 imaging agent with $^{68}$Ga is published in Wester et al, Theranostics, 2015, 5(6):618-30. There remains a need for imaging agents that can provide sensitive and rapid detection of pathological conditions associated with the expression of CXCR4 receptors, in particular of inflammation and cancer metastasis.

Mooring et al. report benzenesulfonamides as CXCR4 inhibitors. Chem Med Chem, 2013, 8(4):622-32. See also U.S. Published Patent Application No. 2013/13849646, WO 2008/109154, WO 2005/042489, and CAS Registry Number 1394738-93-2 and 1646745-83-6.

References cited herein are not an admission of prior art.

SUMMARY

This disclosure relates to methylsulfonamide derivatives and uses as imaging agents and other uses related to CXCR4 inhibition. In certain embodiments, the disclosure relates to pharmaceutical compositions comprising compounds disclosed herein, derivatives, or pharmaceutically acceptable salts or prodrugs thereof. In certain embodiments, the compositions disclosed herein are used for imaging to study CXCR4 related conditions.

In certain embodiments, the methylsulfonamide derivative is a compound having formula I

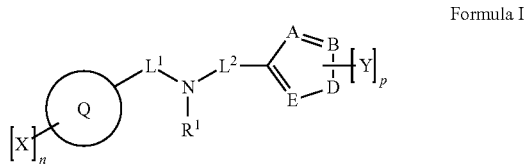

Formula I or salts, esters, prodrugs, or derivatives thereof wherein, wherein substituents are reported herein.

In certain embodiments, the compounds of formula I comprise a radionuclide such as at least one a radionuclide selected from the group consisting of $^{11}$C, $^{13}$N, $^{18}$F, $^{76}$Br, $^{123}$I, $^{124}$I, $^{125}$I, and $^{131}$I.

In certain embodiments, the disclosure relates to pharmaceutical compositions comprising a compound disclosed herein and a pharmaceutically acceptable excipient optionally comprising another active agent.

In certain embodiments, the disclosure relates to imaging methods comprising a) administering compound comprising a radionuclide as disclose herein to a subject; and b) scanning the subject for emissions and further comprising the step of detecting the emissions and creating an image indicating or highlighting the location of the compound containing radionuclide in the subject.

In certain embodiments, the disclosure relates to a pharmaceutical composition comprising a compound as described herein including salts and prodrugs thereof and a pharmaceutically acceptable excipient, diluent, or carrier. In certain embodiments, the pharmaceutical composition is in the form of a tablet, pill, capsule, gel, or aqueous buffered solution.

In certain embodiments, the disclosure relates to kits comprising compounds disclosed herein.

In certain embodiments, the disclosure relates to uses of compounds disclosed herein in the production of a medicament for the treatment of CXCR4 related conditions, such as, viral infections, abnormal cellular proliferation, retinal degeneration, inflammatory diseases, or as an immunostimulant or immunosuppressant.

In certain embodiments, the disclosure relates to pharmaceutical compositions comprising a compound as described herein and another active ingredient such as a chemotherapeutic agent.

In certain embodiments, the disclosure relates to methods of treating or preventing cancer comprising administering pharmaceutical composition comprising a compound as described herein optionally in combination with another active ingredient to a subject in need thereof. In further embodiments, the subject is at risk of, exhibiting symptoms of, or diagnosed with cancer.

In certain embodiments, the disclosure relates to uses of a compound as described herein in the production of a medicament for the treatment of CXCR4 related conditions.

In certain embodiments, the disclosure relates to methods of making compounds disclosed herein comprising mixing starting materials and reagents under conditions such that the product is formed.

In other embodiments, $L^1$ is —C(O)—, —S(O)—, —S(O)$_2$—, —N(R)—C(O)—, —N(R)—S(O)—, —N(R)—S(O)$_2$—, -alkylene-N(R)—C(O)—, -alkylene-N(R)—S(O)—, or -alkylene-N(R)—S(O)$_2$—; $L^2$ is alkylene, —C(O)—, —S(O)—, —S(O)$_2$—, or a covalent bond; A, B, D, E: independently C or N or O or S or N—N or C=C (can be single or double bond i.e. N—N or N=N, C—C or C=C i.e., 6-membered ring p=5, the A=C, B=C, D=C2, E=C); $R^1$ is hydrogen, substituted or unsubstituted alkyl, substituted or unsubstituted alkenyl, substituted or unsubstituted alkynyl, alkoxy, alkoxyalkyl, alkoxyacyl, haloalkyl, cyanoalkyl, hydroxyalkyl, thioalkyl, alkylthioalkyl, substituted or unsubstituted aminoalkyl, substituted or unsubstituted aminoacylalkyl, substituted or unsubstituted amino, substituted or unsubstituted arylamino, substituted or unsubstituted heteroarylamino, substituted or unsubstituted imidoyl, substituted or unsubstituted acyl, substituted or unsubstituted arylacyl, substituted or unsubstituted heteroarylacyl, substituted or unsubstituted aminoacyl, substituted or unsubstituted arylalkyl, substituted or unsubstituted heteroarylalkyl, substituted or unsubstituted heterocyclylalkyl, substituted or unsubstituted aryl, substituted or unsubstituted heteroaryl, substituted or unsubstituted cycloalkyl, substituted or unsubstituted cycloalkylalkyl, substituted or unsubstituted heterocyclyl, or —S(O)$_2$—R$_z$, wherein R$_z$ is selected from the group consisting of substituted or unsubstituted alkyl, substituted or unsubstituted arylalkyl, substituted or unsubstituted heteroarylalkyl, substituted or unsubstituted aryl, or substituted or unsubstituted heteroaryl; X and Y are independently hydrogen, halogen, —R, —OR, —CN, —OR-halogen, —N(R$_x$R$_y$), Nacylamino, —SR, —S$_2$R, —S(O)—R, —S(O)$_2$—R$_x$, —SNHR, —S$_2$NHR, —SN(R$_x$R$_y$), —S$_2$N(R$_x$R$_y$), —S(O)$_2$—N(R$_x$R$_y$), —C(O)—R, —C(O)N(R$_x$R=), —C(O)$_2$—R, and —C(O)$_2$—N(R$_x$R$_y$); wherein R$_x$ and R$_y$ are independently selected from R; n is 0, 1, 2, 3, 4 or 5; p is 0, 1, 2, 3, 4 or 5. In the context of imaging agents at least one of X and Y includes a radioisotope selected from the group consisting of $^{11}$C, $^{13}$N, $^{18}$F, $^{76}$Br, $^{123}$I, $^{124}$I, $^{125}$I.

Figure 1:
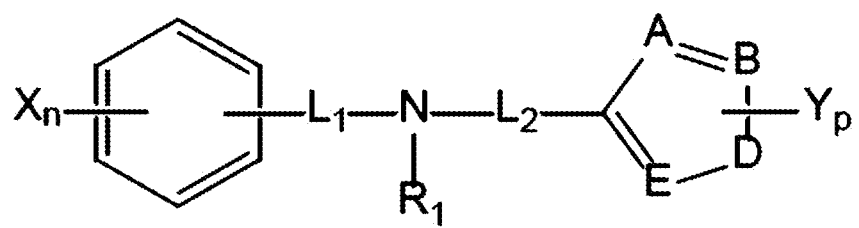
FIG. 1 illustrates an embodiment of this disclosure. In certain embodiments, it is contemplated that L1, L2 are substituted or unsubstituted alkylene or —C(O)— or —S(O)— or —S(O)$_2$— or covalent bond (nitrogen can be directly linked to aryl group. In these case L=covalent bond). A, B, D, E are independently C or N or O or S or N—N. $R^1$ is independently selected from H, straight chain, branched or cyclic alkyl, aralkyl, aryl heteroaryl, acyl (RC—) and imidoyl (RC(NH)— or RC(NR')—) groups. X, Y are each independently H, R, acyl, F, CI, Br, I, OH, OR, NH$_2$, NHR, NR$_2$, SR, S$_2$R, S—NHR, S$_2$—NHR, S—NRR', S$_2$—NRR', NHacyl, N(acyl)$_2$, CO$_2$H, CO$_2$R, CONRR' or CN, where R and R' are independently selected from straight chain, branched or cyclic alkyl, alkenyl, alkynyl, aminoalkyl, heteroalkyl, haloalkyl, aralkyl, alkoxyalkyl, cyanoalkyl, hydroxyalkyl, thioalkyl, N-alkylaminoalkyl, N,N-dialkylaminoalkyl, alkylthioalkyl, aryl, heteroarylalkyl, heterocyclylalkyl, alkoxyaryl, and haloalkoxyaryl; wherein at least one of X and Y includes a radionuclide selected from the group consisting of $^{11}$C, $^{13}$N, $^{18}$F, $^{76}$Br, $^{123}$I, $^{124}$I, $^{125}$I. The "n" is 0, 1, 2 or 3. The "p" is 0, 1, 2 or 3.
Figure 2:
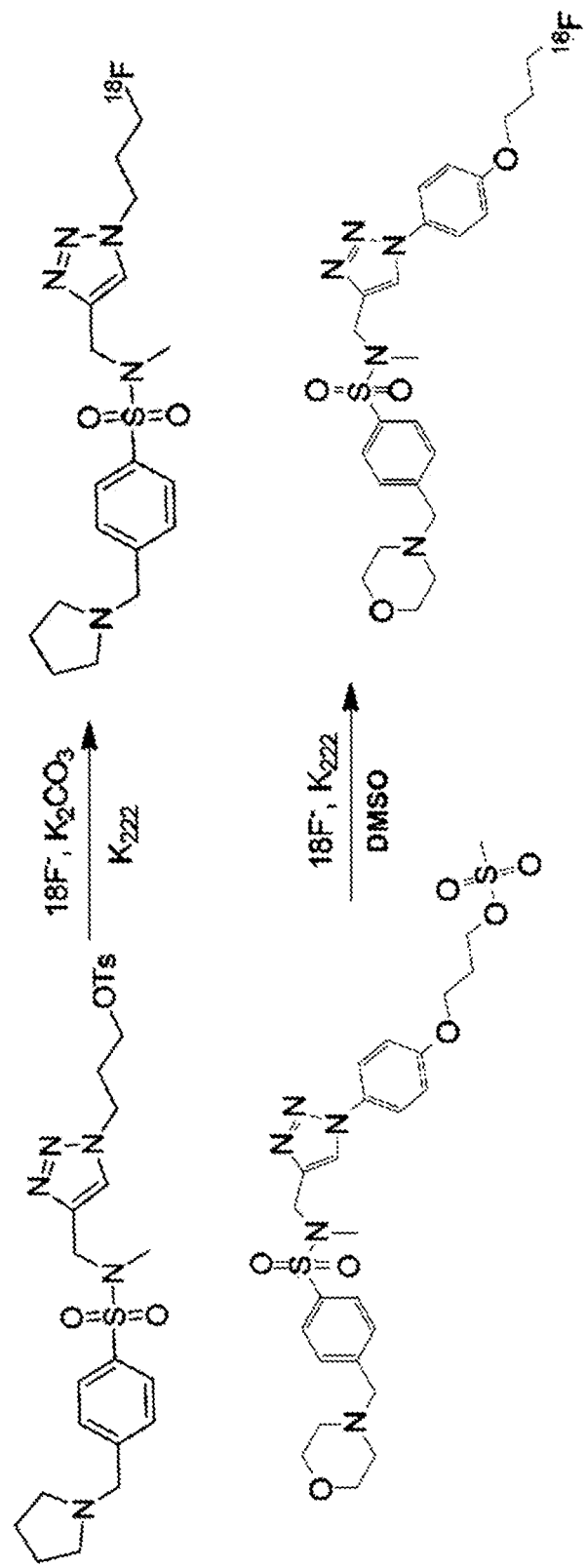

FIG. 2 illustrates the preparation of an embodiment of the disclosure. No-carrier-added [$^{18}$F]F— was obtained through the nuclear reaction $^{18}$O(p, n)$^{18}$F by irradiation of $^{18}$O-enriched water. After the delivery of [$^{18}$F]F— from the cyclotron, the radioactivity was passed through an anion exchange resin cartridge to trap [$^{18}$F]F—. [$^{18}$F]F— was then eluded with potassium carbonate solution into a vessel containing Kryptofix 2,2,2 (K222) and the mixture was dried by azeotropic distillation with acetonitrile. The precursor was dissolved in anhydrous acetonitrile and added to the dried K222/K[$^{18}$F]F. The mixture was heated at 120° C. for 20 min to produce [$^{18}$F] product. The crude reaction mixture was purified by HPLC (Prep column, methanol/water=1/1), then the collected fraction was trapped on C$_{18}$ solid phase extraction cartridge and eluted by ethanol into a vial containing isotonic saline. The [$^{18}$F] product in saline solution was sterilized by filtration through a 0.2 micron filter for further study.

Figure 3:
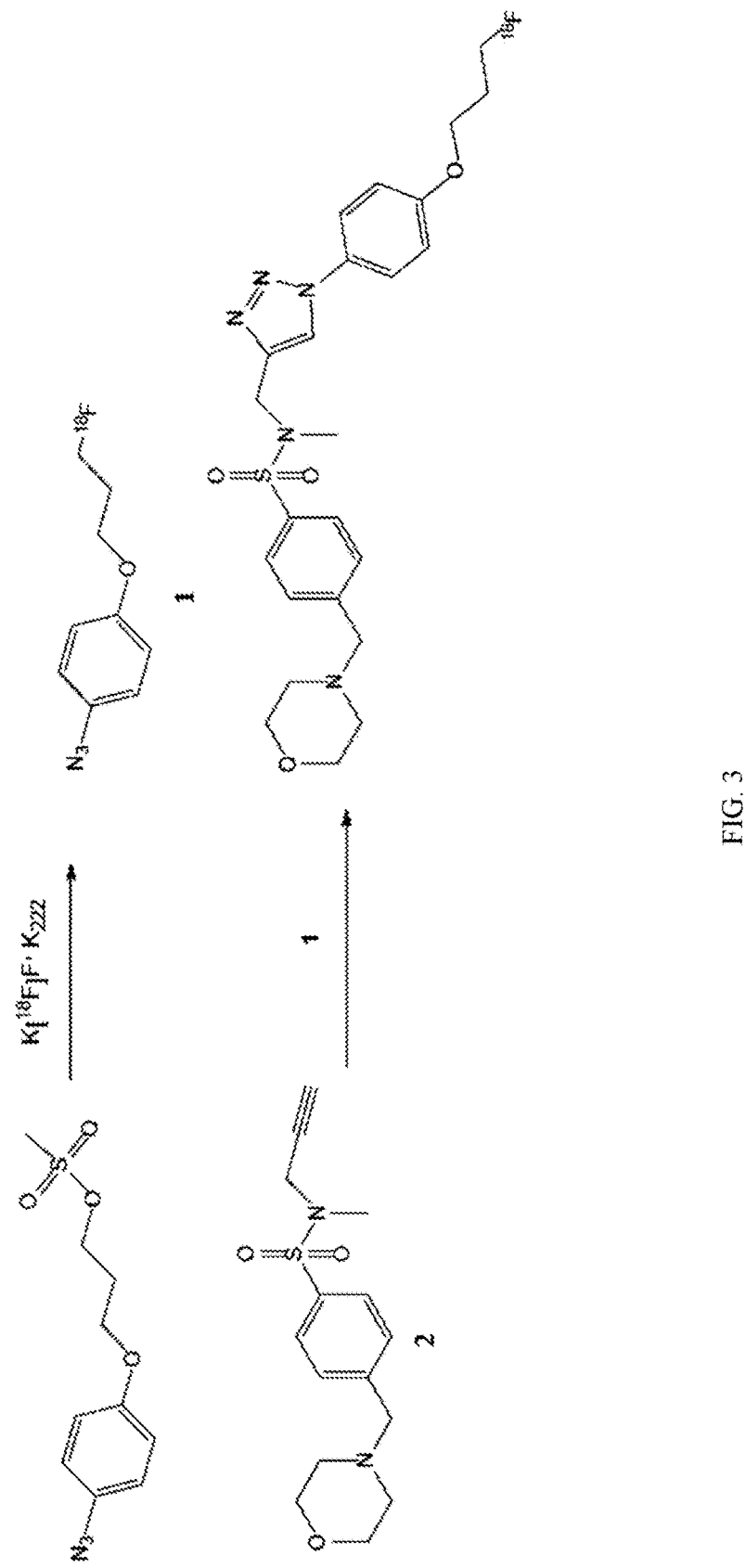

FIG. 3 illustrates the preparation of certain embodiments of this disclosure. The compound 1 can be labeled with the same procedure as described above. Reaction under conditions of the click reaction (e.g., addition of CuSO$_4$ with sodium ascorbate to the mixture of compound 1 and 2), the [$^{18}$F] product can be produced. To produce non-radioactive compounds, one can mix the mesylate intermediate dissolved in tert-butanol with cesium fluoride and reflux the reaction mixture for 3 hrs. After evaporation of solvent, final product was obtained by column chromatography.

Figure 4:
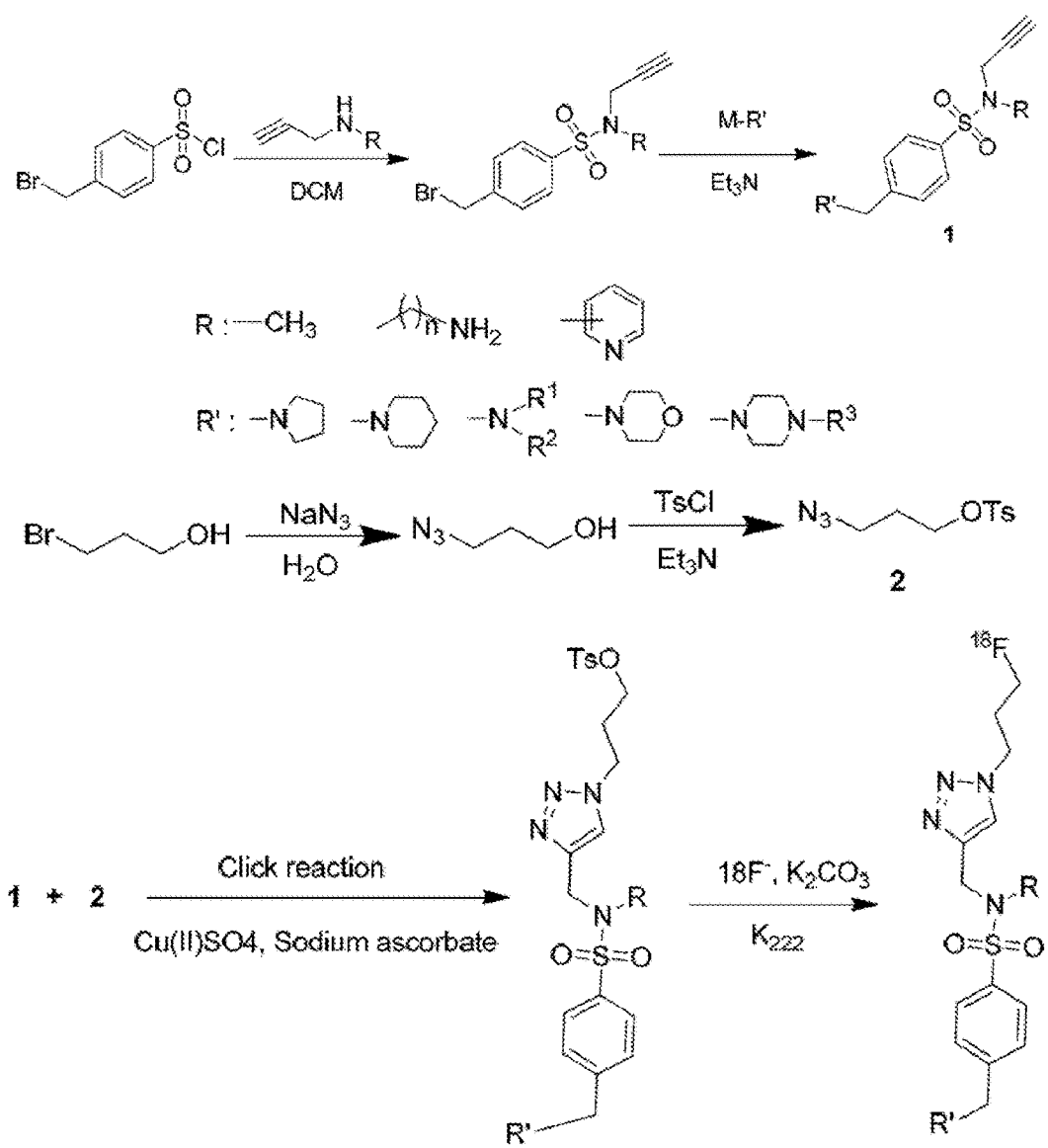

FIG. 4 illustrates the preparation of certain embodiments of this disclosure.

Figure 5:
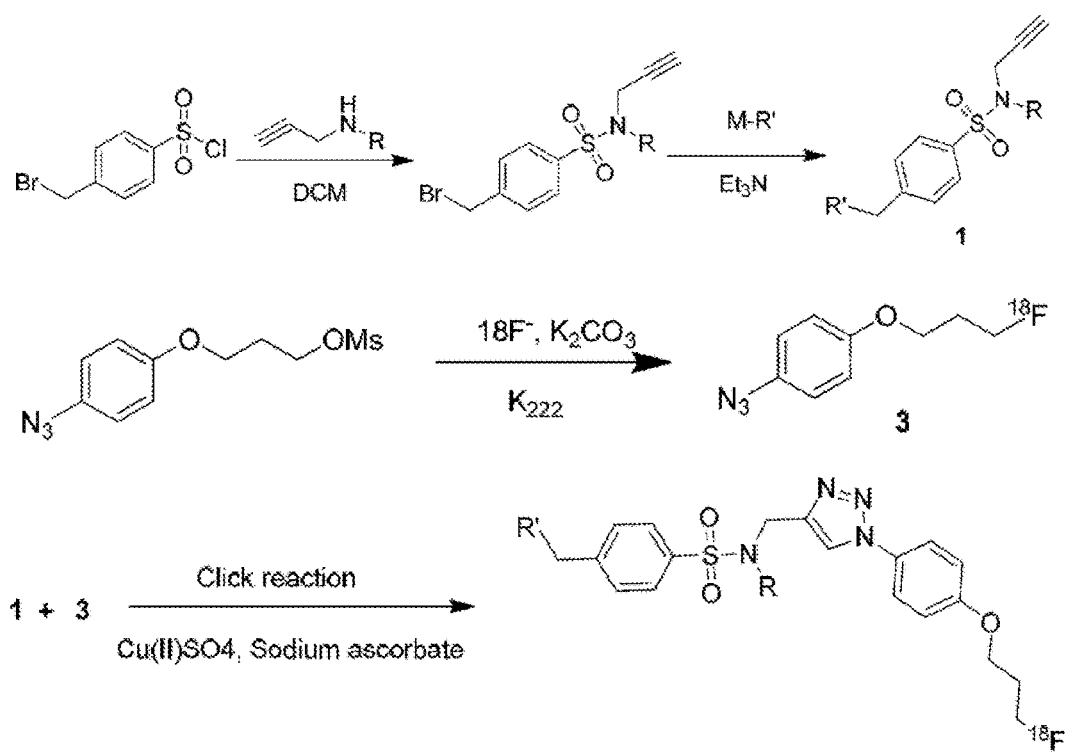

FIG. 5 illustrates the preparation of certain embodiments of this disclosure.

Figure 6:
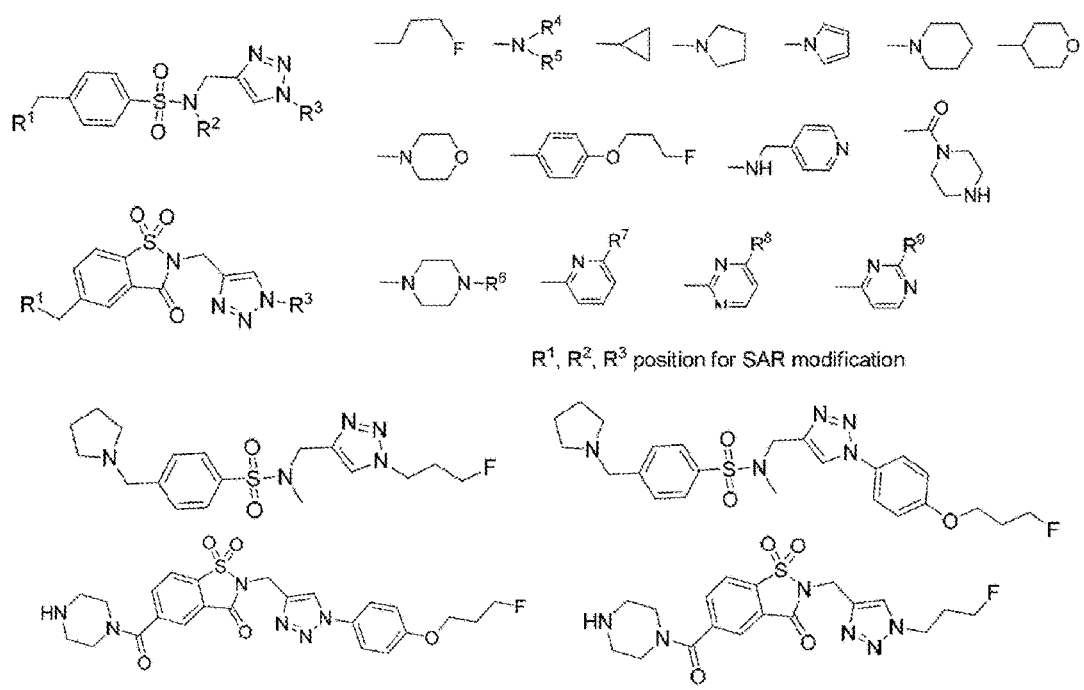

FIG. 6 illustrates certain embodiments of the disclosure.

Figure 7A:
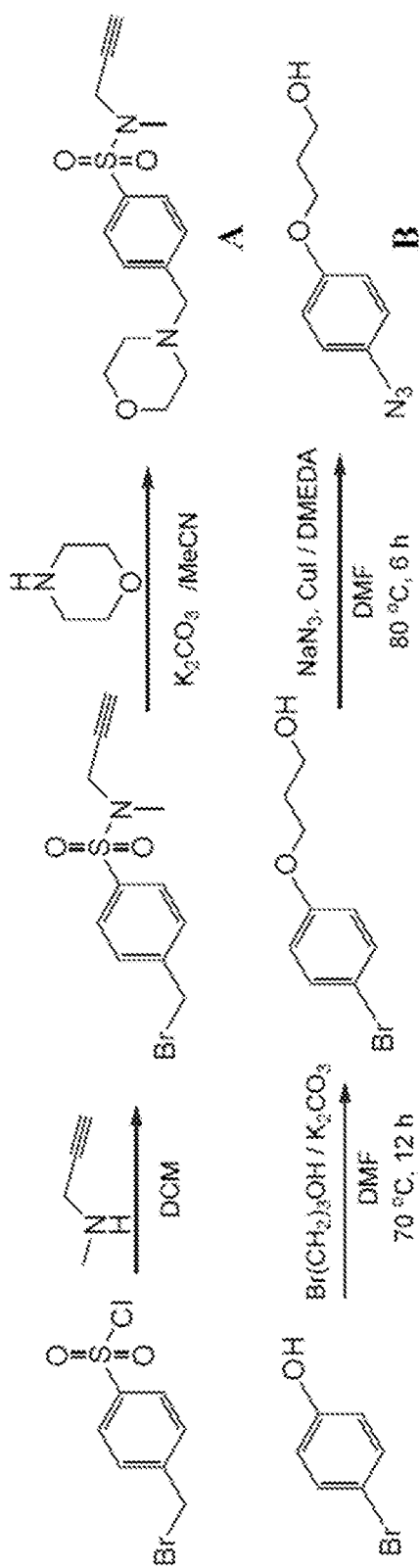

FIG. 7A illustrates the preparation of certain embodiments of this disclosure.

Figure 7B:
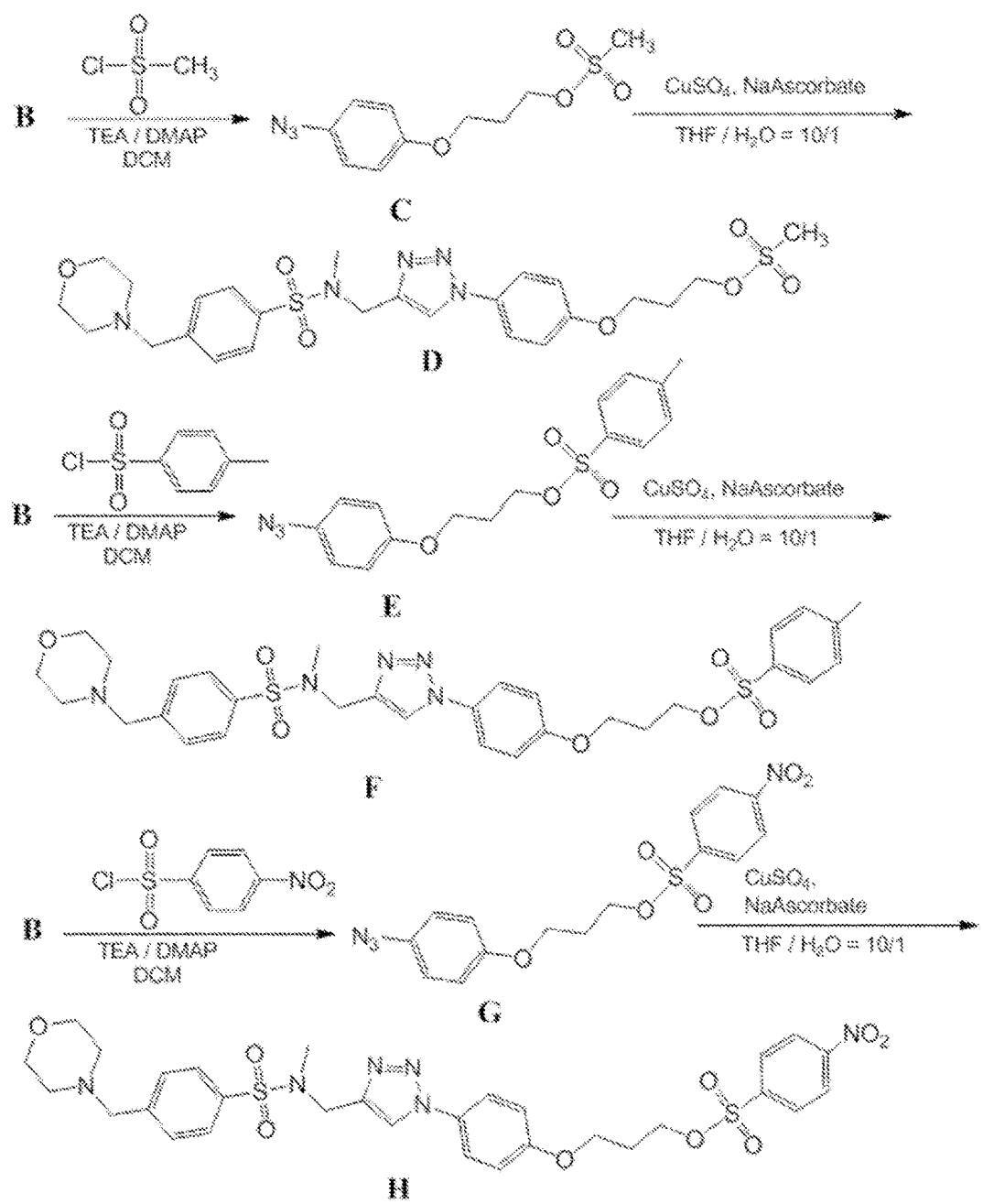

FIG. 7B illustrates the preparation of certain embodiments of this disclosure.

Figure 8:
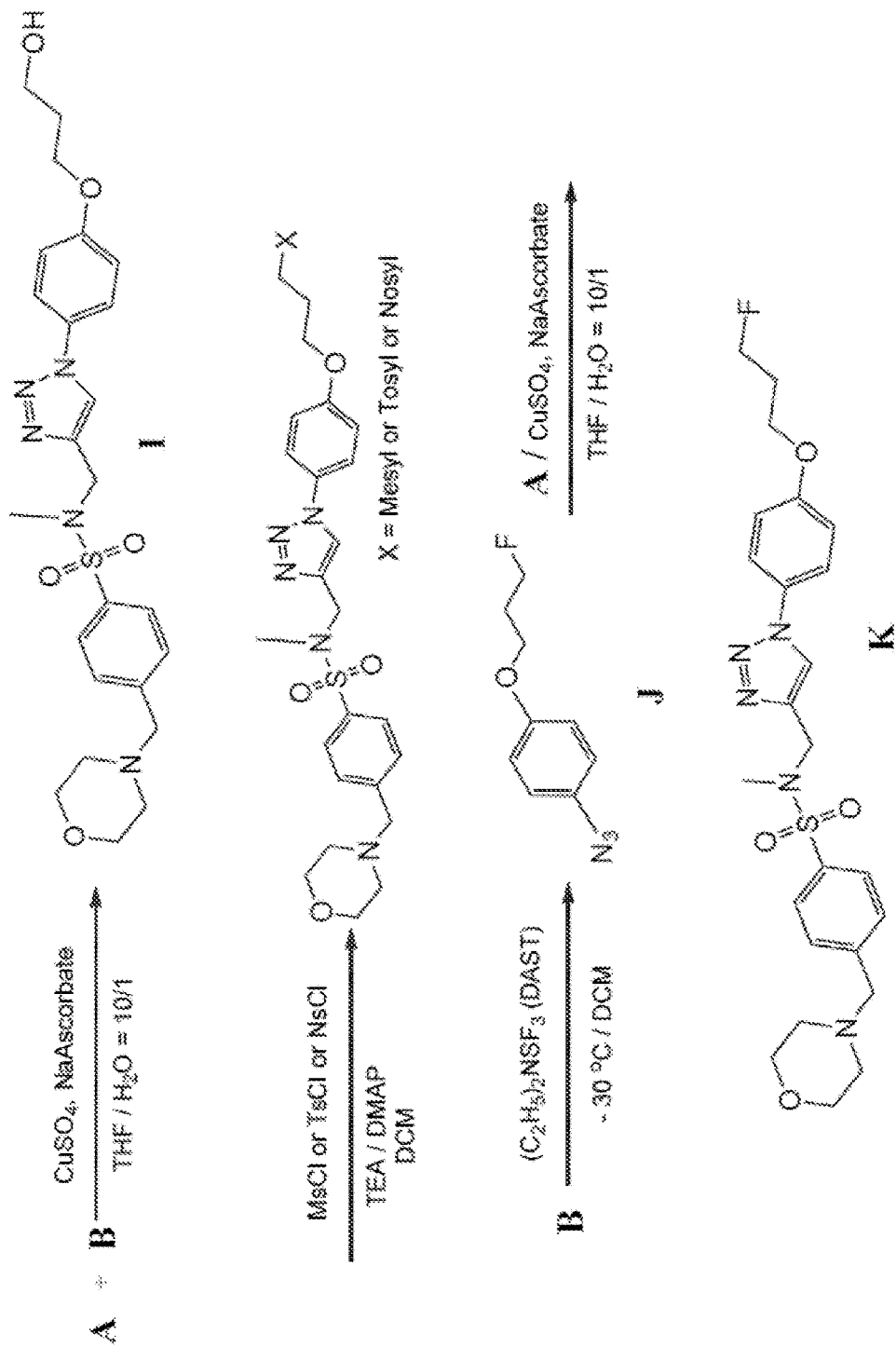

FIG. 8 illustrates the preparation of certain embodiments of this disclosure.

Figure 9:
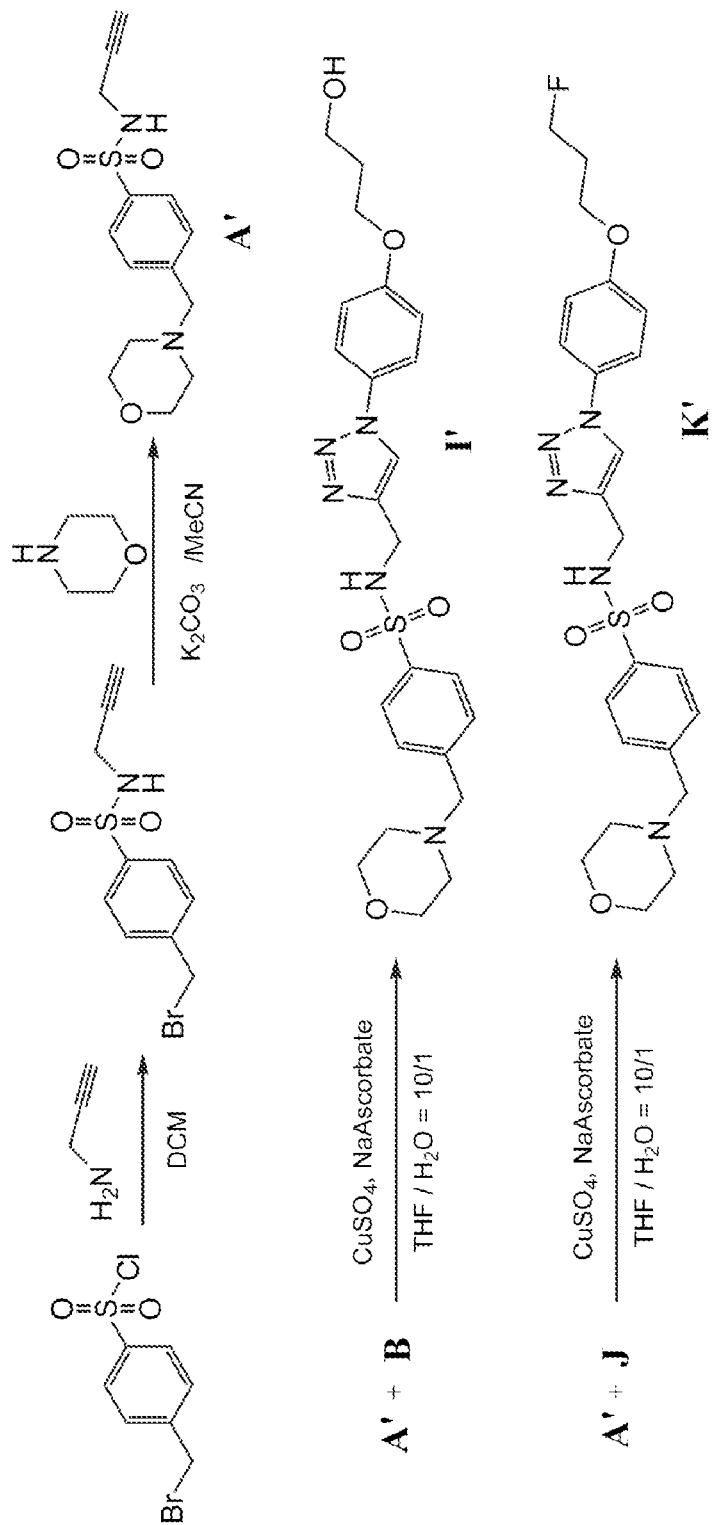

FIG. 9 illustrates the preparation of certain embodiments of this disclosure.

Figure 10:
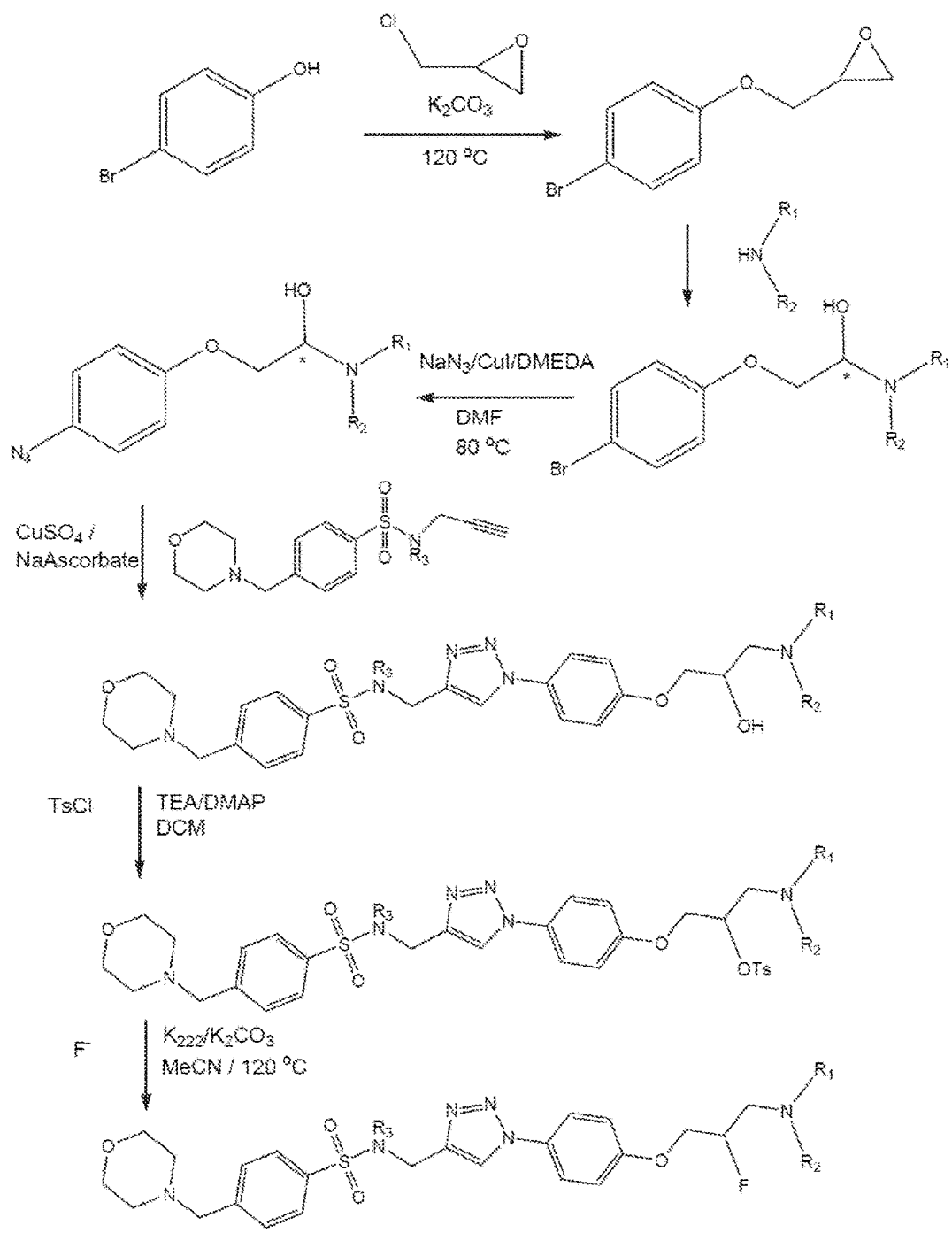

FIG. 10 illustrates the preparation of certain embodiments of this disclosure. In certain embodiments, $R^1$ and $R^2$ are methyl. In certain embodiments, $R^1$ and $R^2$ are ethyl. In certain embodiments, $R^1$ and $R^2$ are alkyl. In certain embodiments, $R^1$ is alkyl and $R^2$ is hydrogen. In certain embodiments, $R^1$ is hydrogen, alkyl, alkylene glycol, alkanoyl, carbocyclyl, aryl, or heterocyclyl, wherein $R^1$ is optionally substituted; $R^2$ is hydrogen, alkyl, alkylene glycol, alkanoyl, carbocyclyl, aryl, or heterocyclyl, wherein $R^2$ is optionally substituted. In certain embodiments, $R^3$ is hydrogen or alkyl, wherein $R^3$ is optionally substituted. In certain embodiments, F is $^{18}$F.

Figure 11:
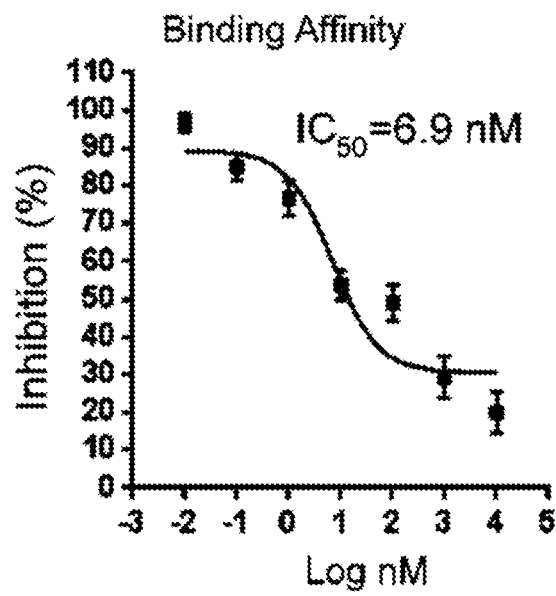
Figure 12:
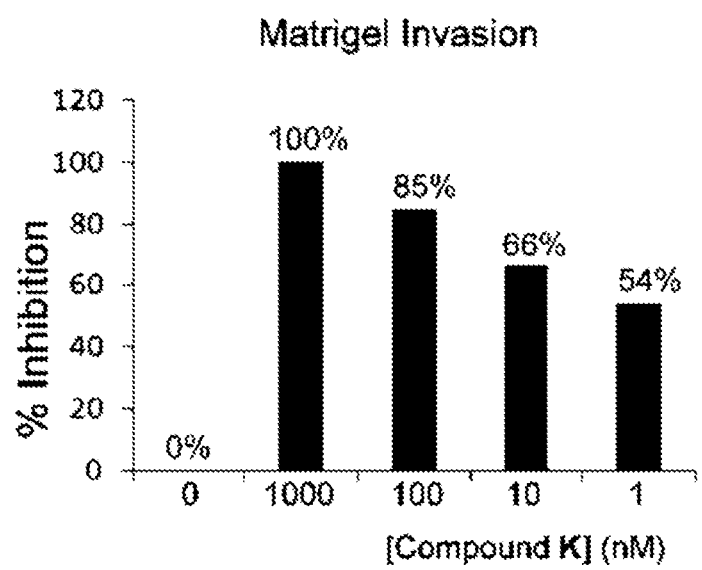
Figure 13:
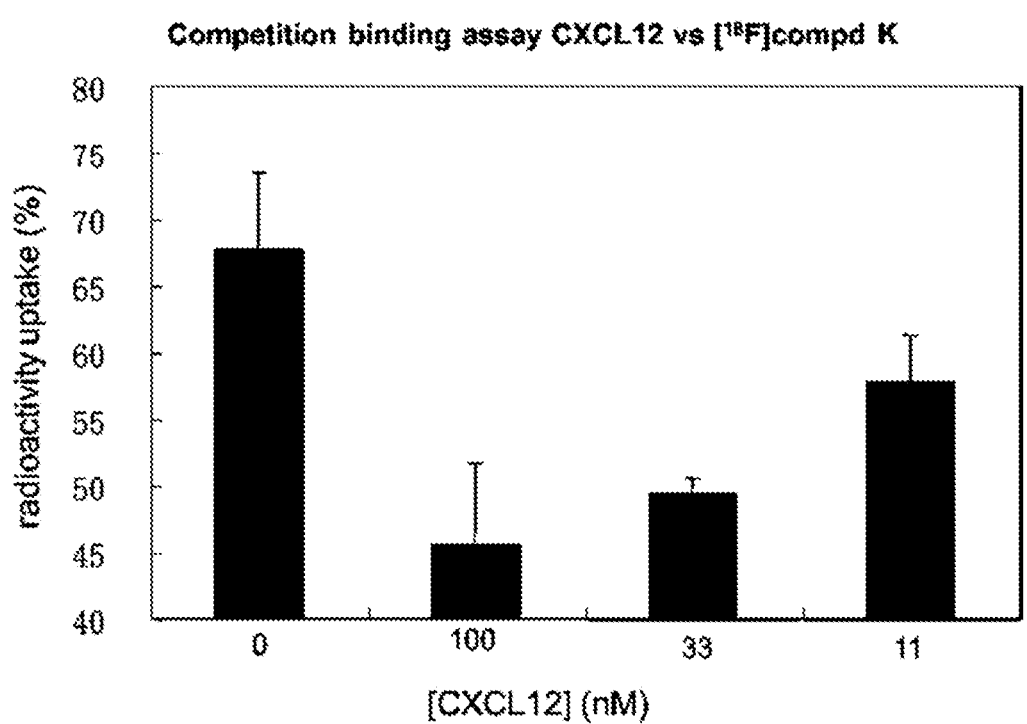
Figure 14:
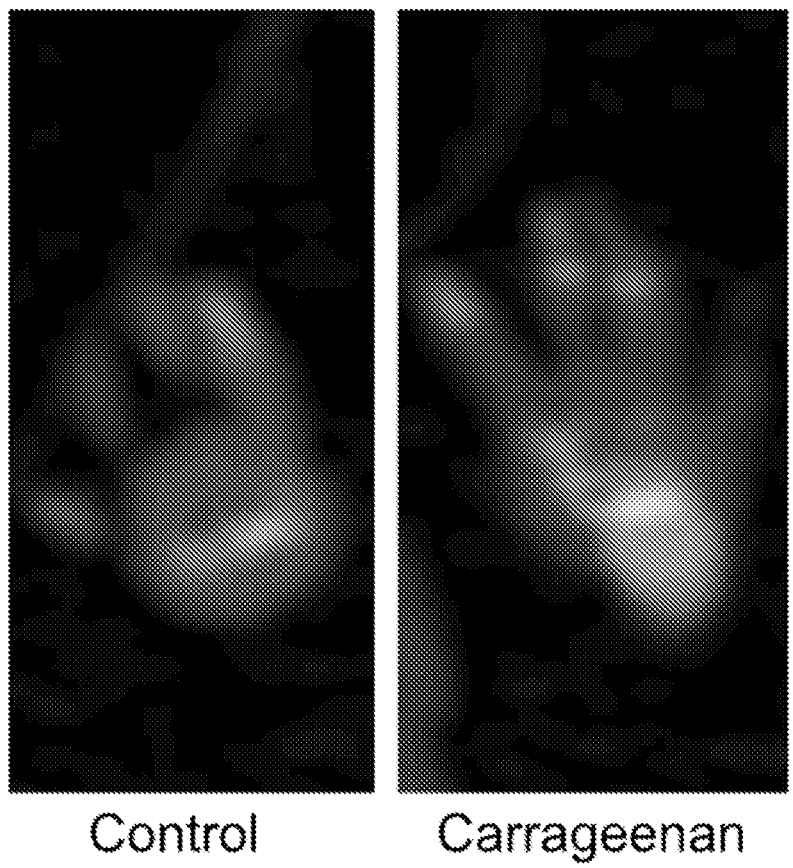
Figure 15:
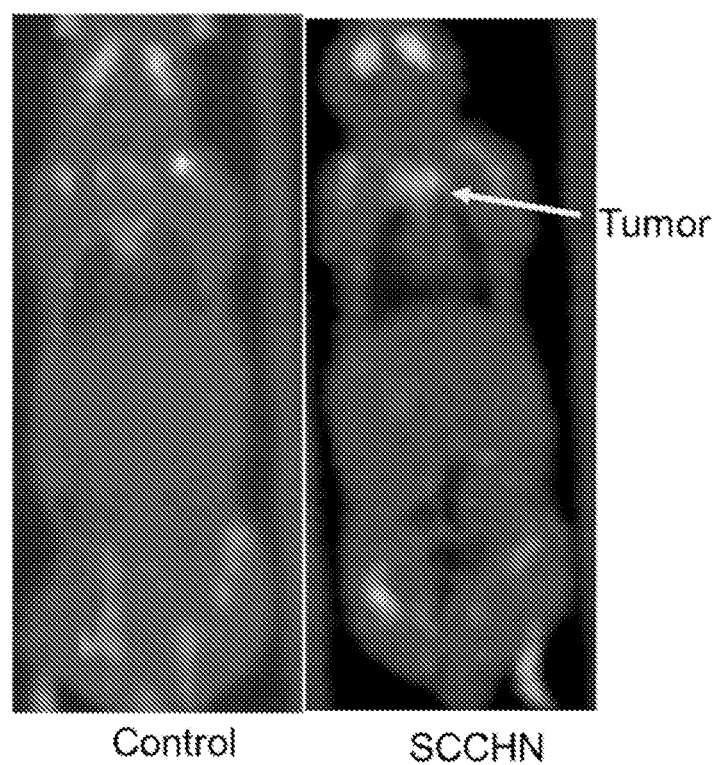
Figure 16:
Figure 17:
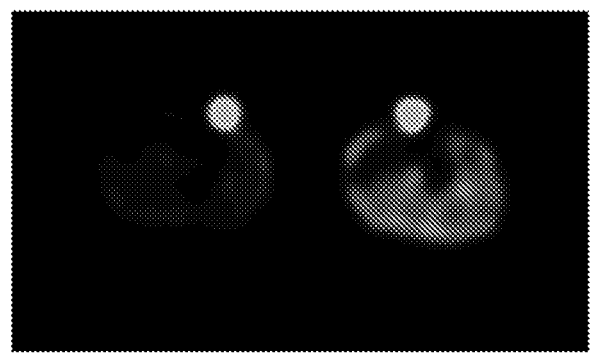

FIG. 11 shows binding affinity data.
FIG. 12 shows Matrigel invasion data.
FIG. 13 shows a competitive binding assay for CXCL12.
FIG. 14 shows paw edema images.
FIG. 15 shows head and neck cancer images.
FIG. 16 shows blocking data.
FIG. 17 shows lung images.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

To the extent that structures provided herein are compounds with tautomers by hydrogen migration, a skilled artisan would understand the formula to cover all tautomeric forms.

As used herein, "alkyl" means a noncyclic straight chain or branched, unsaturated or saturated hydrocarbon such as those containing from 1 to 10 carbon atoms, typically 1 to 4 otherwise designated $C_{1-4}$alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylene glycol" refers to an alkoxy group with a carbon chain of two or more having a terminal hydroxy (i.e., —O—$CH_2CH_2$—OH, —O—$CH_2CH_2CH_2$—OH) or polymers thereof, e.g., polyethylene glycol [—O—$(CH_2CH_2)_n$—OH wherein n is 2 to 10]. In certain embodiments, polyalkylene glycol refers to an alkylene glycol wherein n is 10 to 50, or 10 to 100, or 10 to 500, or 2 to 1,000, or 2 to 5,000, or 100 to 1,000, or 100 to 5,000, or 1,000 to 10,000. Typically polymers are a mixture or distribution of monomers lengths. Thus, in certain embodiments, n is the average number of monomers within a polymer.

"Alkylamino" refers an alkyl group as defined above attached through an amino bridge. An example of an alkylamino is methylamino, (i.e., —NH—$CH_3$).

"Aminoalkyl" refers to an amino group attached through an alkyl bridge as defined above (i.e., $NH_2$-alkyl-).

"Alkanoyl" refers to an alkyl as defined above attached through a carbonyl bride (i.e., —C(=O)alkyl).

"Alkylsulfonyl" refers to an alkyl as defined above attached through a sulfonyl bridge (i.e., —S(=O)$_2$alkyl) such as mesyl and the like, and "arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —NHS(=O)$_2$alkyl), and an "Arylsulfamoyl" refers to an alkyl attached through a sulfamoyl bridge (i.e., —NHS(=O)$_2$aryl).

"Alkylsulfinyl" refers to an alkyl as defined above attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aR_b$, —$NR_aC(=O)OR_b$, —$NR_aSO_2R_b$, —C(=O)$R_a$, —C(=O)$OR_a$, —C(=O)$NR_aR_b$, —OC(=O)$NR_aR_b$, —$OR_a$, —$SR_a$, —$SOR_a$, —S(=O)$_2R_a$, —OS(=O)$_2R_a$ and —S(=O)$_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

"Positron emission tomography" (PET) refers to an imaging technique that produces a three-dimensional image by detecting pairs of gamma rays emitted indirectly by a positron-emitting radionuclide tracer. Three-dimensional images of tracer concentration within the area are then constructed by computer analysis. A radioactive tracer is administered to a subject e.g., into blood circulation. Typically there is a waiting period while tracer becomes concentrated in areas of interest; then the subject is placed in the imaging scanner. As the radionuclide undergoes positron emission decay, it emits a positron, an antiparticle of the electron with opposite charge, until it decelerates to a point where it can interact with an electron, producing a pair of (gamma) photons moving in approximately opposite directions. These are detected in the scanning device. The technique typically utilizes simultaneous or coincident detection of the pair of photons moving in approximately opposite direction (the scanner typically has a built-in slight direction-error tolerance). Photons that do not arrive in pairs (i.e. within a timing-window) are typically ignored. One typically localizes the source of the photons along a straight line of coincidence (also called the line of response, or LOR). This data is used to generate an image.

The term "radionuclide" or "radioactive isotope" refers to molecules of enriched isotopes that exhibit radioactive decay (e.g., emitting positrons). Such isotopes are also referred to in the art as radioisotopes. A radionuclide tracer does not include radioactive primordial nuclides, but does include a naturally occurring isotopes that exhibit radioactive decay with an isotope distribution that is enriched, e.g., is several fold greater than natural abundance. In certain embodiments, is contemplated that the radionuclides are limited to those with a half live of less than 1 hour and those with a half-life of more than 1 hour but less than 24 hours. Radioactive isotopes are named herein using various commonly used combinations of the name or symbol of the element and its mass number (e.g., $^{18}$F, F-18, or fluorine-18). Elements that can be used in the compounds of the present disclosure include: F-18; C-11; N-13 1-125, 1-124, 1-131 and 1-123; Cl-32, Cl-33, Cl-34; Br-74, Br-75, Br-76, Br-77, Br-78; Re-186, Re-188; Y-90, Y-86; Lu-177 and Sm-153. Typical radioactive isotopes include 1-124, F-18 fluoride, C-11, N-13, and O-15, which have half-lives of 4.2 days, 110 minutes, 20 minutes, 10 minutes and 2 minutes, respectively. Preferably, the radioactive isotopes used in the present method include F-18, C-11, N-13, I-123, I-124, I-127, I-131, Br-76, Cu-64, Tc-99m, Y-90, Ga-67, Cr-51, Ir-192, Mo-99, Sm-153 and Tl-201. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

Methods of preparing radiolabeled ligands are well known in the art. Example of such methods are disclosed in, for example: 1) Jewett, D. M. (1992) A Simple Synthesis of [$^{11}$C]Methyl Triflate Appl. Radiat. Isot. 43, 1383-1385; 2) Crouzel, C. Langstrom, B., Pike, V. W., and Coenen, H. H. (1987) Recommendations for a practical production of [$^{11}$C] methyl iodide Appl. Radiat. Isot. Int. J. Appl. Instrum. Part A 38, 601-603; Dannals, R. F., Ravert, H. T.; 3) Wilson, A. A. (1990) Radiochemistry of Tracers for Neurotransmitter Receptor Studies. In: Quantitative Imaging: Neuroreceptors, Neurotransmitters, and Enzymes. (Edited by Frost), J. J. Wagner Jr., H. N. pp. 19-35, Raven Press, New York; 4) Jewett, D. M., Manger, T. J., and Watkins, G. L. (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York; 5) Marazano, C., Maziere, M., Berger, G., and Comar, D. (1977) Synthesis of methyl iodide-$^{11}$C and formaldehyde-$^{11}$C Appl. Radiat. Isot. 28, 49-52; 6) Watkins, G., Jewett, D., Mulholland, G., Kitbourn, M., and Toorongian, S. (1988) A Captive Solvent Method for Rapid N-[$^{11}$C]Methylation of Secondary Amides Application to the Benzodiazepine, 4'-Chlorodiazepam (RO5-4864) Appl. Radiat. Isot. 39, 441-444; and 7) Wilson, A. A., DaSilva, J. N., and Houle, S. (1996) In vivo evaluation of [$^{11}$C] and [$^{15}$F]-labeled cocaine analogues as potential dopamine transporter ligands for positron emission tomography Nucl. Med. Biol. 23, 141-146.

Methylsulfonamide Derivatives

In certain embodiments, the disclosure relates to methylsulfonamide derivatives disclosed herein, prodrugs, esters, or salts and compositions thereof. Although it is not intended that certain embodiments of the disclosure be limited by any particular mechanism it is believed that these compounds bind the CXCR4 receptor.

In certain embodiments, methylsulfonamide derivatives have formula I

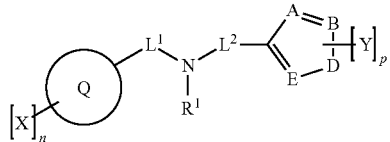

Formula I or salts, esters, prodrugs, or derivatives thereof wherein,

A, B, D, and E are each are each individually and independently C, N, O, S, N2 or C2;

ring Q is a carbocyclyl, aryl, or heterocyclyl;

X is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein X is optionally a radionuclide or optionally substituted with a radionuclide, or optionally substituted with $R^{10}$;

Y is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein Y is optionally a radionuclide or optionally substituted with a radionuclide, or optionally substituted with $R^{10}$ wherein $R^{10}$ is a radionuclide or $R^{10}$ is substituted with a radionuclide;

n is 0, 1, 2, 3, 4, or 5 and p is 0, 1, 2, 3, or 4 provided that the sum of n and p must be greater than 1 or 2;

$L^1$ and $L^2$ are each individually and independently linking groups comprising one or more bridging groups selected from a covalent bond, —[CH$_2$]—, —[CH$_2$CH$_2$]—, —[CH=CH]—, —O—, —NH—, —S—, —C(O)—, —S(O)—, and —S(O)$_2$— (nitrogen is able to linked directly to Q or heterocyclic ring (A,B,D,E,C).

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^1$ and an atom within ring Q form a heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

For any of the embodiments disclosed herein, the compounds of formula I comprises a positron-emitting radionuclide.

For any of the embodiments disclosed herein, X is a heterocyclylalkyl. For any of the embodiments disclosed herein, X is alkyl substituted with R10 is heterocyclyl.

For any of the embodiments disclosed herein, Y is alkyl or alkoxy terminally substituted with a halogen, a positron-emitting halogen, a hydroxy, tosyl, mesyl, alkylsulfonyl ester or arylsulfonyl ester or derivative thereof.

For any of the embodiments disclosed herein, Y is a radionuclide, $^{18}F$, halogen or alkyl or alkoxy terminally substituted with $^{18}F$, halogen, hydroxyl, thiol, —O-p-toluenesulfonyl, —O-p-bromobenzenesulfonyl, —O-(2- or 4)-nitrobenzene sulfonyl, —O-methanesulfonyl, —O-trifluoromethanesulfonyl, —O-5(dimethylamino)naphthalene-1-sulfonyl, —S-p-toluenesulfonyl, —S-p-bromobenzenesulfonyl, —S-(2- or 4)-nitrobenzene sulfonyl, —S-methanesulfonyl, —S— trifluoromethanesulfonyl, —S-5(dimethylamino)naphthalene-1-sulfonyl.

In certain embodiments, the compound of formula I has formula IA,

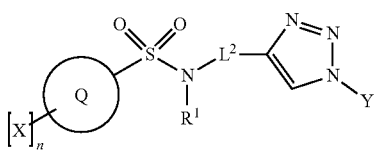

Formula IA or salts, esters, prodrugs, or derivatives thereof wherein, ring Q is a carbocyclyl, aryl, or heterocyclyl;

X is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein X is optionally a radionuclide or optionally substituted with a radionuclide, or optionally substituted with $R^{10}$;

Y is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein Y is optionally a radionuclide or optionally substituted with a radionuclide, or optionally substituted with $R^{10}$ wherein $R^{10}$ is a radionuclide or $R^{10}$ is substituted with a radionuclide;

n is 0, 1, 2, 3, 4, or 5;

$L^2$ is a covalent bond or a linking groups comprising one or more bridging groups selected from —[CH$_2$]—, —[CH$_2$CH$_2$]—, —[CH=CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^1$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

In certain embodiments, the compound of formula I has formula IB or formula IC,

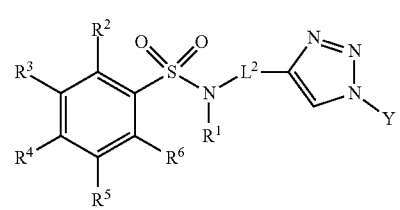

Formula IB

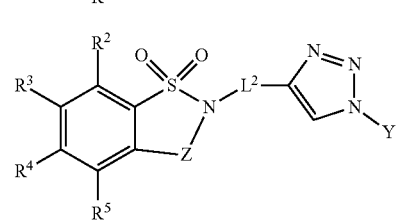

Formula IC or salts, esters, prodrugs, or derivatives thereof wherein,

Z is CH$_2$, NH, O, S, or C=O;

$R^2$, $R^3$, $R^4$, $R^5$, and $R^6$, are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$, $R^3$, $R^4$, $R^5$, and $R^6$, are optionally substituted with one or more, the same or different, $R^{10}$;

Y is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein Y is a radionuclide or optionally substituted with a radionuclide, or optionally substituted with $R^{10}$ wherein $R^{10}$ is a radionuclide or $R^{10}$ is substituted with a radionuclide;

$L^2$ is a covalent bond or a linking group comprising one or more bridging groups selected from —[CH$_2$]—, —[CH$_2$CH$_2$]—, —[CH=CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

In certain embodiments, the compound of formula I has formula ID or formula IE,

Formula ID

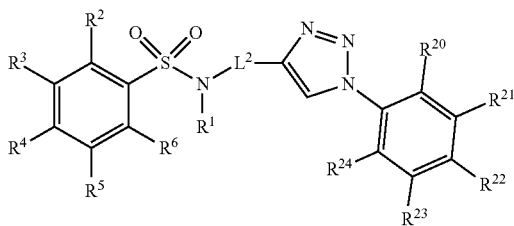

-continued

Formula IE

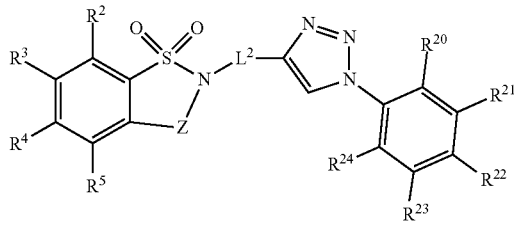

or salts, esters, prodrugs, or derivatives thereof wherein,

Z is CH$_2$, NH, O, S, or C=O;

$R^2$, $R^3$, $R^4$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$, $R^3$, $R^4$, $R^5$, and $R^6$, are optionally substituted with one or more, the same or different, $R^{10}$;

$R^{20}$, $R^{21}$, $R^{22}$, $R^{23}$, and $R^{24}$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{20}$, $R^{21}$, $R^{22}$, $R^{23}$, and $R^{24}$ are optionally substituted with a radionuclide, or optionally substituted with $R^{30}$ wherein $R^{30}$ is a radionuclide or $R^{30}$ is substituted with a radionuclide;

$L^2$ is a covalent bond or a linking group comprising one or more bridging groups selected from —[CH$_2$]—, —[CH$_2$CH$_2$]—, —[CH=CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{31}$;

$R^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{31}$ is optionally substituted with one or more, the same or different, $R^{32}$; and $R^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

For any of the embodiments disclosed herein, $R^{22}$ is alkyl or alkoxy terminally substituted with a halogen, a positron-emitting halogen, a hydroxy, tosyl, mesyl, alkylsulfonyl ester or arylsulfonyl ester or derivative thereof.

For any of the embodiments disclosed herein, $R^{22}$ may be a radionuclide, $^{18}$F, halogen or alkyl or alkoxy terminally substituted with radionuclide, $^{18}$F, halogen, hydroxyl, thiol, —O-p-toluenesulfonyl, —O-p-bromobenzenesulfonyl, —O-(2- or 4)-nitrobenzene sulfonyl, —O-methanesulfonyl, —O-trifluoromethanesulfonyl, —O-5(dimethylamino)naphthalene-1-sulfonyl, —S-p-toluenesulfonyl, —S-p-bromobenzenesulfonyl, —S-(2- or 4)-nitrobenzene sulfonyl, —S-methanesulfonyl, —S-trifluoromethanesulfonyl, —S—S(dimethylamino)naphthalene-1-sulfonyl.

In certain embodiments, the compound of formula I has formula IF or formula IG,

Formula IF

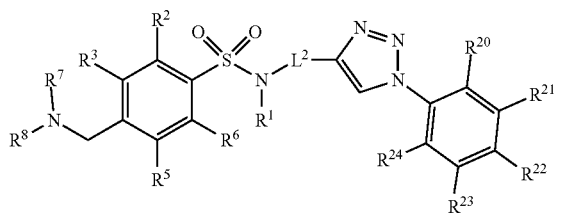

Formula IG

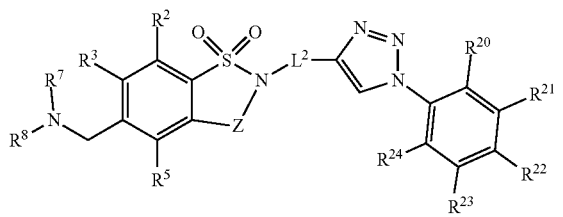

or salts, esters, prodrugs, or derivatives thereof wherein,

Z is CH$_2$, NH, O, S, or C═O;

$R^2$, $R^3$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$, $R^3$, $R^5$, and $R^6$, are optionally substituted with one or more, the same or different, $R^{10}$;

$R^7$ and $R^8$ form a heterocyclyl optionally substituted with one or more, the same or different, $R^{10}$; or $R^7$ and $R^8$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^7$ and $R^8$, are optionally substituted with one or more, the same or different $R^{10}$;

$R^{20}$, $R^{21}$, $R^{22}$, $R^{23}$, and $R^{24}$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{20}$, $R^{21}$, $R^{22}$, $R^{23}$, and $R^{24}$ are optionally a radionuclide or optionally substituted with a radionuclide, or optionally substituted with $R^{30}$ wherein $R^{30}$ is a radionuclide or $R^{30}$ is substituted with a radionuclide;

$L^2$ is a covalent bond or a linking group comprising one or more bridging groups selected from —[CH$_2$]—, —[CH$_2$CH$_2$]—, —[CH═CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{31}$;

$R^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{31}$ is optionally substituted with one or more, the same or different, $R^{32}$; and $R^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

In certain embodiments, the compound of formula I has formula IH or formula II,

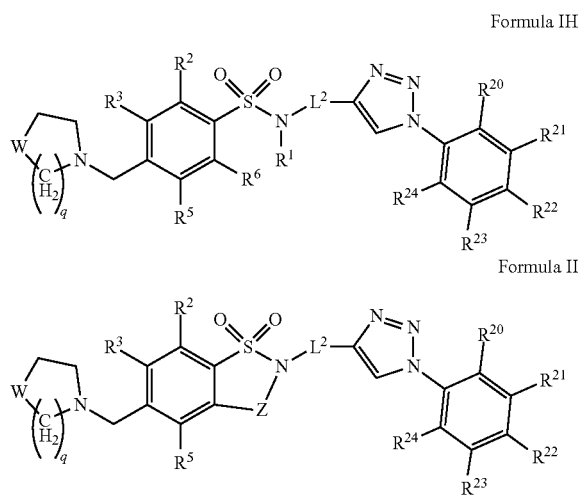

Formula IH

Formula II or salts, esters, prodrugs, or derivatives thereof wherein, q is 1 or 2;

W is O, S, C=O, NR$^{25}$, or CR$^{25}$R$^{26}$;

Z is CH$_2$, NH, O, S, or C=O;

$R^2$, $R^3$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$, $R^3$, $R^5$, and $R^6$, are optionally substituted with one or more, the same or different, $R^{10}$;

$R^7$ and $R^8$ form a heterocyclyl optionally substituted with one or more, the same or different, $R^{10}$; or $R^7$ and $R^8$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^7$ and $R^8$, are optionally substituted with one or more, the same or different $R^{10}$;

$R^{20}$, $R^{21}$, $R^{22}$, $R^{23}$, $R^{24}$, $R^{25}$, and $R^{26}$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{20}$, $R^{21}$, $R^{22}$, $R^{23}$, $R^{24}$, $R^{25}$, and $R^{26}$ optionally substituted with a radionuclide, or optionally substituted with $R^{30}$ wherein $R^{30}$ is a radionuclide or $R^{30}$ is substituted with a radionuclide;

$L^2$ is a covalent bond or a linking group comprising one or more bridging groups selected from —[CH$_2$]—, —[CH$_2$CH$_2$]—, —[CH=CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl;

$R^{30}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{31}$;

$R^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{31}$ is optionally substituted with one or more, the same or different, $R^{32}$; and $R^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

In certain embodiments, the compound of formula I has formula IJ or formula IK,

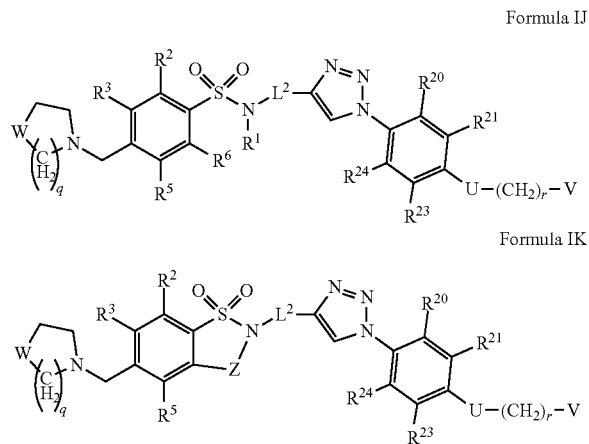

Formula IJ

Formula IK or salts, esters, prodrugs, or derivatives thereof wherein, q is 1 or 2;

r is 1, 2, 3, 4, 5, 6, 7, or 8;

U is O, S, NH, or $CH_2$;

W is O, S, C=O, $NR^{25}$, Or $CR^{25}R^{26}$;

V is a radionuclide;

Z is $CH_2$, NH, O, S, or C=O;

$R^2$, $R^3$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^2$, $R^3$, $R^5$, and $R^6$, are optionally substituted with one or more, the same or different, $R^{10}$;

$R^7$ and $R^8$ form a heterocyclyl optionally substituted with one or more, the same or different, $R^{10}$; or $R^7$ and $R^8$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^7$ and $R^8$, are optionally substituted with one or more, the same or different $R^{10}$;

$R^{20}$, $R^{21}$, $R^{22}$, $R^{23}$, $R^{24}$, $R^{25}$, and $R^{26}$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{20}$, $R^{21}$, $R^{22}$, $R^{23}$, $R^{24}$, $R^{25}$, and $R^{26}$ optionally substituted with a radionuclide, or optionally substituted with $R^{30}$ wherein $R^{30}$ is a radionuclide or $R^{30}$ is substituted with a radionuclide;

$L^2$ is a covalent bond or a linking group comprising one or more bridging groups selected from —[CH$_2$]—, —[CH$_2$CH$_2$]—, —[CH=CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl;

$R^{30}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{31}$;

$R^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{31}$ is optionally substituted with one or more, the same or different, $R^{32}$; and $R^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

In certain embodiments, the compound of formula I has formula IL or formula IM,

Formula IL

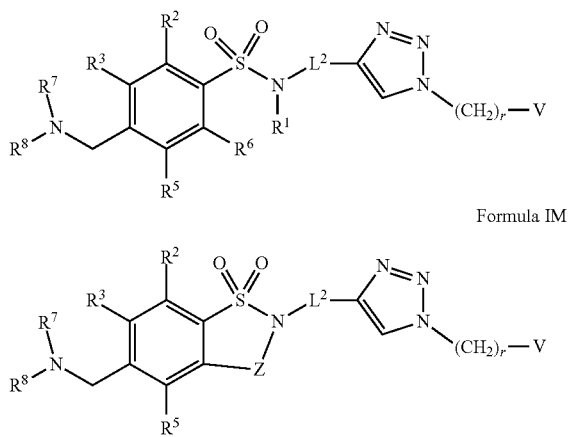

Formula IM or salts, esters, prodrugs, or derivatives thereof wherein,
r is 1, 2, 3, 4, 5, 6, 7, or 8;
V is a radionuclide;
Z is $CH_2$, NH, O, S, or C=O;
$R^2$, $R^3$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, $(alkyl)_2$amino, alkylsulfinyl, alkylsulfonyl, arylsulfonyl, carbocyclyl, aryl, or heterocyclyl, wherein $R^2$, $R^3$, $R^5$, and $R^6$, are optionally substituted with one or more, the same or different, $R^{10}$;
$R^7$ and $R^8$ form a heterocyclyl optionally substituted with one or more, the same or different, $R^{10}$; or $R^7$ and $R^8$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, $(alkyl)_2$amino, alkylsulfinyl, alkylsulfonyl, arylsulfonyl, carbocyclyl, aryl, or heterocyclyl, wherein $R^7$ and $R^8$, are optionally substituted with one or more, the same or different $R^{10}$;
$L^2$ is a covalent bond or a linking group comprising one or more bridging groups selected from —[$CH_2$]—, —[$CH_2CH_2$]—, —[CH=CH]—, —O—, —NH—, —S—, —C(O)—, —S(O)—, and —S(O)$_2$—;
$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, $(alkyl)_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, $(alkyl)_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;
$R^{10}$ is alkyl, halogen, nitro, cyano, hydroxy, amino, mercapto, formyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, $(alkyl)_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;
$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

In certain embodiments, the compound of formula I has formula IN or formula IO,

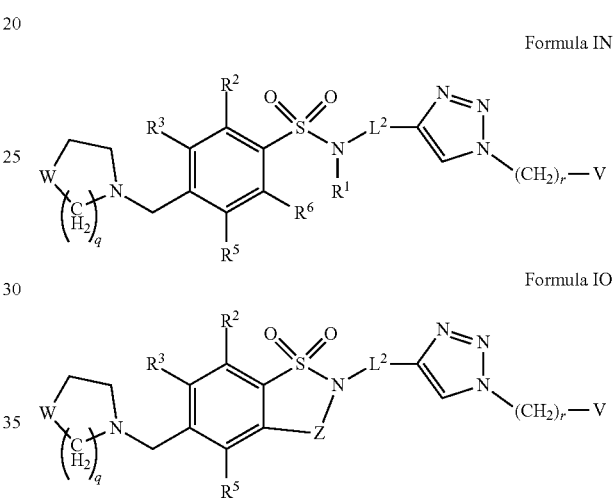

Formula IN

Formula IO or salts, esters, prodrugs, or derivatives thereof wherein,
q is 1 or 2;
r is 1, 2, 3, 4, 5, 6, 7, or 8;
W is O, S, C=O, $NR^{25}$, or $CR^{25}R^{26}$;
V is a radionuclide;
Z is $CH_2$, NH, O, S, or C=O;
$R^2$, $R^3$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, $(alkyl)_2$amino, alkylsulfinyl, alkylsulfonyl, arylsulfonyl, carbocyclyl, aryl, or heterocyclyl, wherein $R^2$, $R^3$, $R^5$, and $R^6$, are optionally substituted with one or more, the same or different, $R^{10}$;
$R^{25}$ and $R^{26}$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, $(alkyl)_2$amino, alkylsulfinyl, alkylsulfonyl, arylsulfonyl, carbocyclyl, aryl, or heterocyclyl, wherein $R^{25}$ and $R^{26}$ optionally substituted with a radionuclide, or optionally substituted with $R^{30}$ wherein $R^{30}$ is a radionuclide or $R^{30}$ is substituted with a radionuclide;
$L^2$ is a covalent bond or a linking group comprising one or more bridging groups selected from —[$CH_2$]—, —[$CH_2CH_2$]—, —[CH=CH]—, —O—, —NH—, —S—, —C(O)—, —S(O)—, and —S(O)$_2$—;
$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$; or $R^1$ is hydrogen; or $R^1$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl;

$R^{30}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{30}$ is optionally substituted with one or more, the same or different, $R^{31}$;

$R^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{31}$ is optionally substituted with one or more, the same or different, $R^{32}$; and $R^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethyl sulfamoyl, N-methyl-N-ethylsulfamoyl, carbocyclyl, aryl, or heterocyclyl.

For any of the embodiments disclosed herein, V is a halogen, a positron-emitting halogen, a hydroxy, tosyl, mesyl, alkylsulfonyl ester or arylsulfonyl ester or derivative thereof.

In certain embodiments, for any of the formula provided herein V is a radionuclide, $^{18}F$, halogen or alkyl or alkoxy terminally substituted with $^{18}F$, halogen, hydroxyl, thiol, —O-p-toluenesulfonyl, —O-p-bromobenzenesulfonyl, —O-(2- or 4)-nitrobenzene sulfonyl, —O-methanesulfonyl, —O-trifluoromethanesulfonyl, —O-5(dimethylamino)naphthalene-1-sulfonyl, —S-p-toluenesulfonyl, —S-p-bromobenzenesulfonyl, —S-(2- or 4)-nitrobenzene sulfonyl, —S-methanesulfonyl, —S-trifluoromethanesulfonyl, —S—S(dimethylamino)naphthalene-1-sulfonyl.

In certain embodiments, the compound of formula I has formula

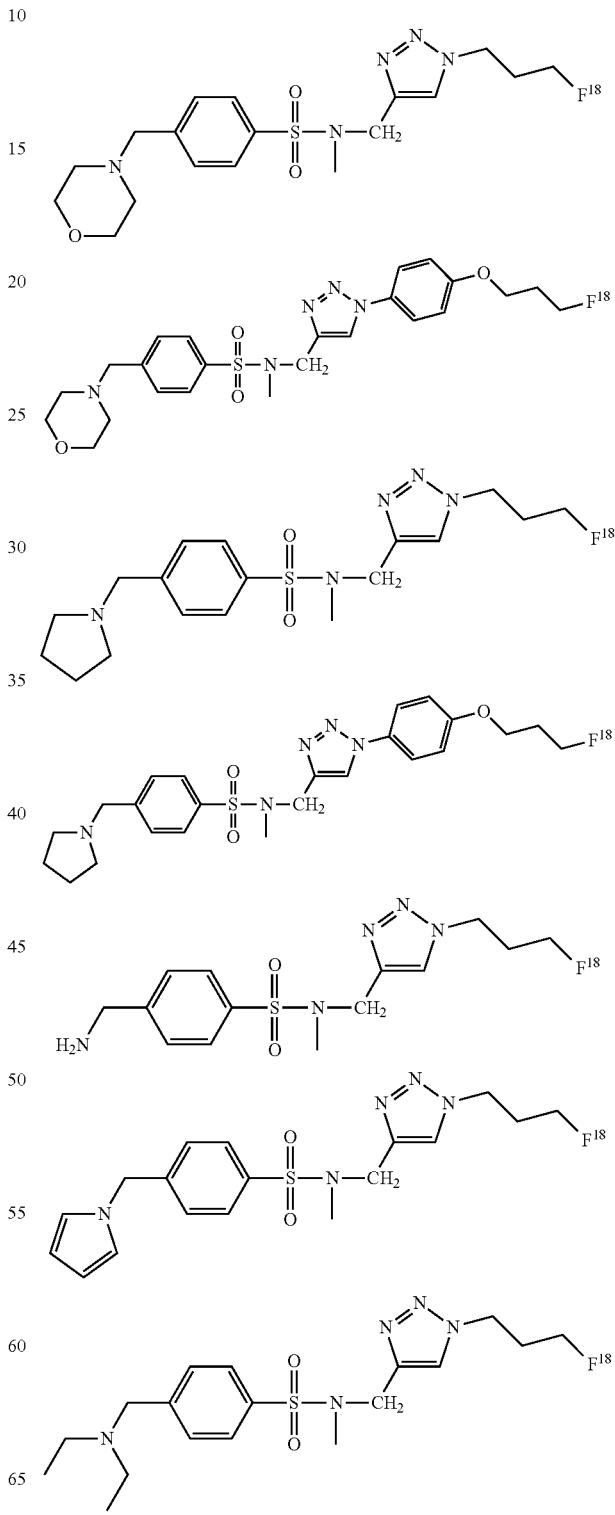

-continued

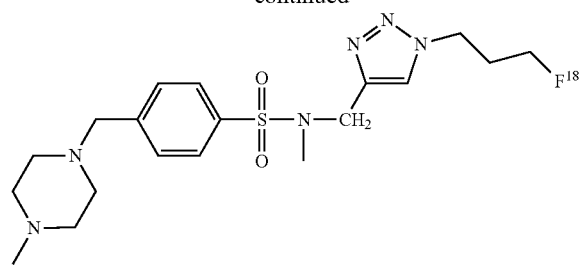
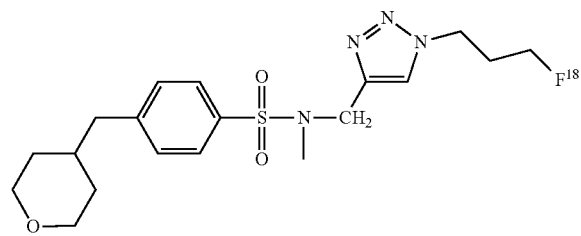
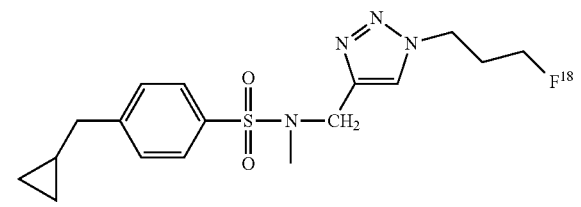
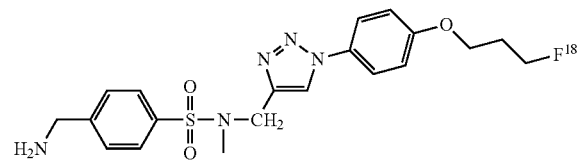
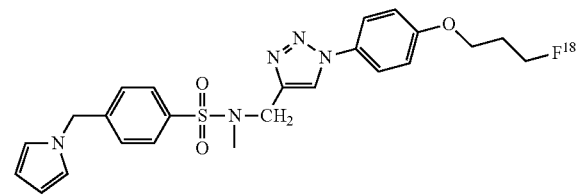
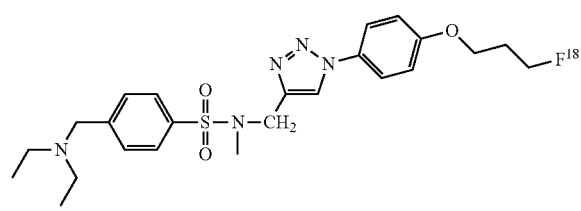
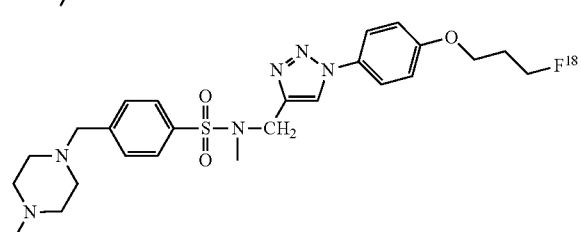
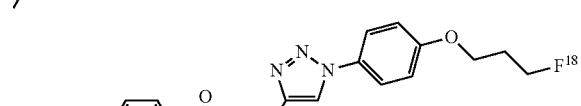
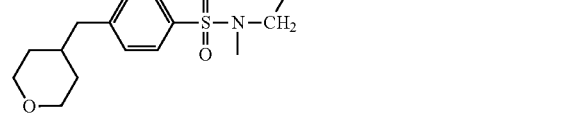

-continued

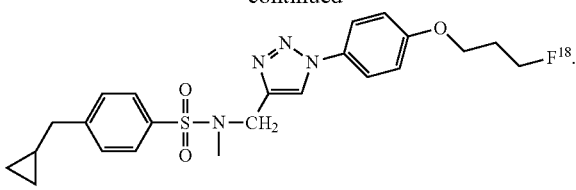

Methods of Production

In certain embodiments, the disclosure relates to methods of making compounds of formula IA as reported herein, Formula IA

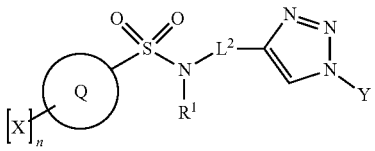

comprising mixing the following alkyne and azide compounds:

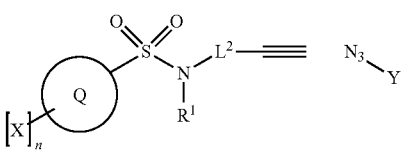

under conditions such that that a compound of formula IA is formed.

In certain embodiments, the disclosure relates to methods of making compounds of formula IB or formula IC as reported herein, Formula IB

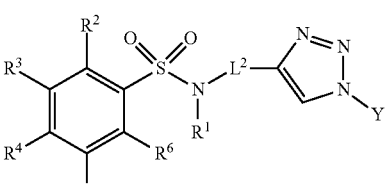

Formula IC

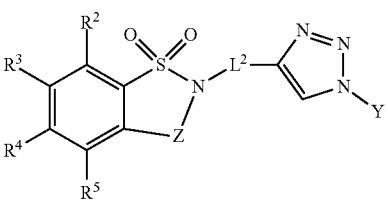

comprising mixing the following alkyne and azide compounds:

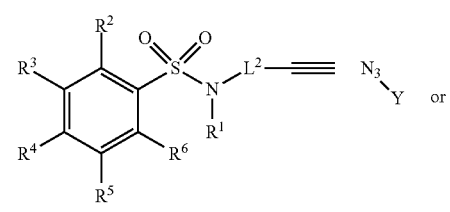

-continued

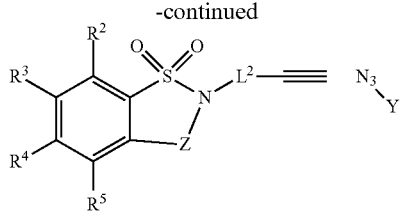

under conditions such that that a compound of formula IB or IC is formed.

In certain embodiments, the disclosure relates to methods of making compounds of formula ID or formula IE as reported herein, Formula ID

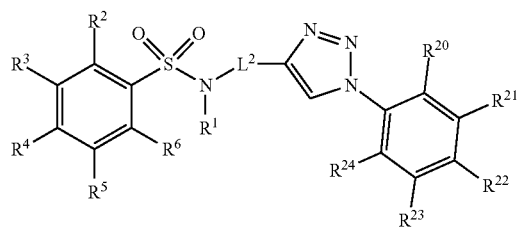

Formula IE

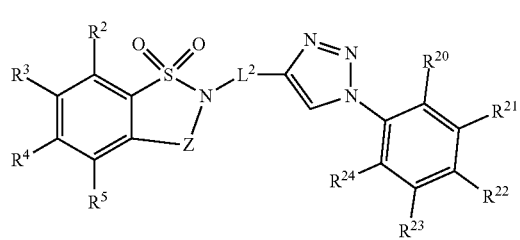

comprising mixing the following alkyne and azide compounds:

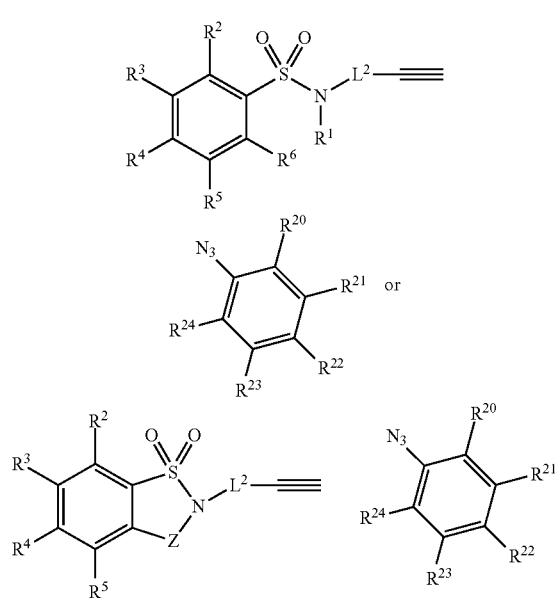

under conditions such that a compound of formula ID or IE is formed.

In certain embodiments, the disclosure relates to methods of making compounds of formula IF or formula IG as reported herein, Formula IF

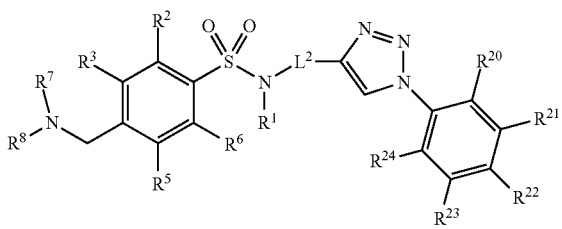

Formula IG

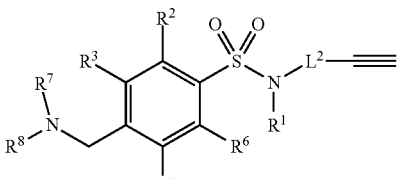

comprising mixing the following alkyne and azide compounds:

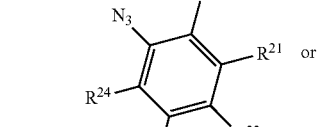

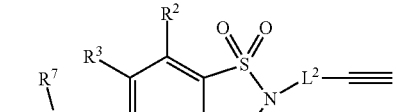

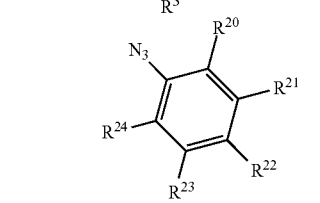

under conditions such that that a compound of formula IF or IG is formed.

In certain embodiments, the disclosure relates to methods of making compounds of formula IH or formula II as reported herein, Formula IH

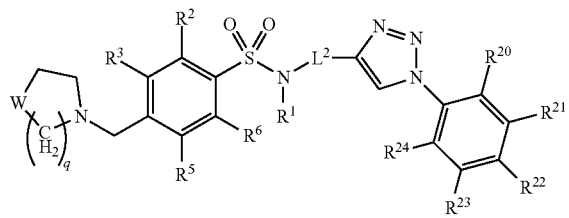

Formula II

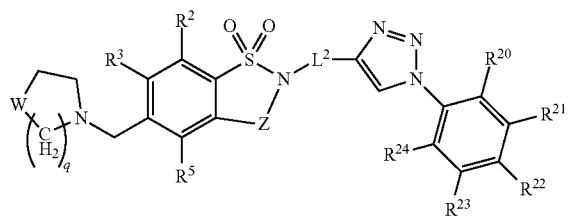

comprising mixing the following alkyne and azide compounds:

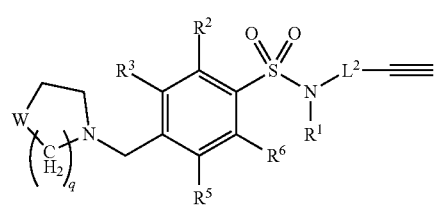

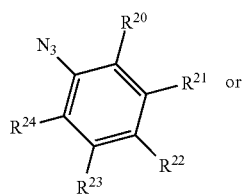

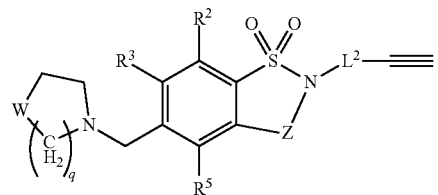

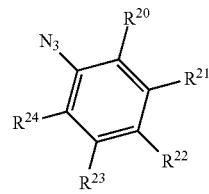

under conditions such that that a compound of formula IH or II is formed.

In certain embodiments, the disclosure relates to methods of making compounds of formula IJ or formula IK as reported herein, Formula IJ

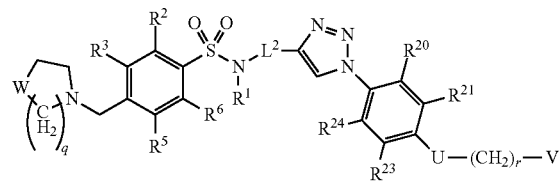

Formula IK

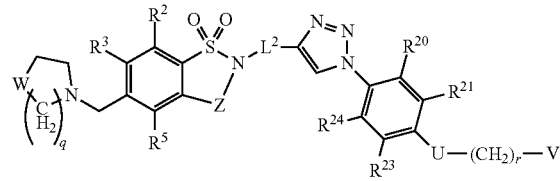

comprising mixing the following alkyne and azide compounds:

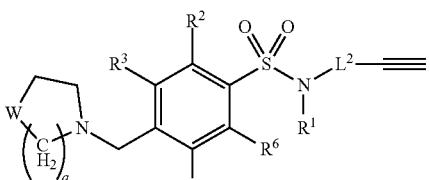

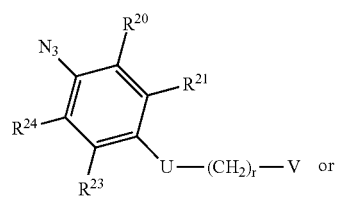

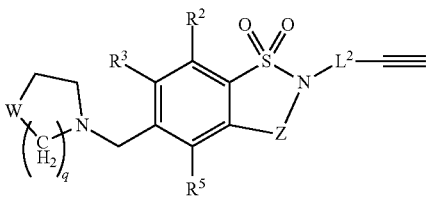

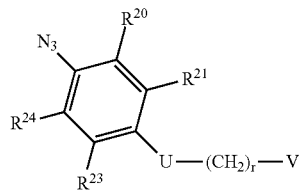

under conditions such that that a compound of formula IJ or IK is formed.

In certain embodiments, the disclosure relates to methods of making compounds of formula IL or formula IM as reported herein, Formula IL
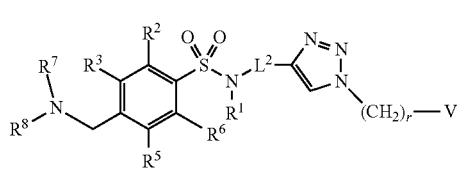

Formula IM
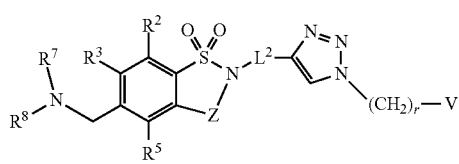

comprising mixing the following alkyne and azide compounds:

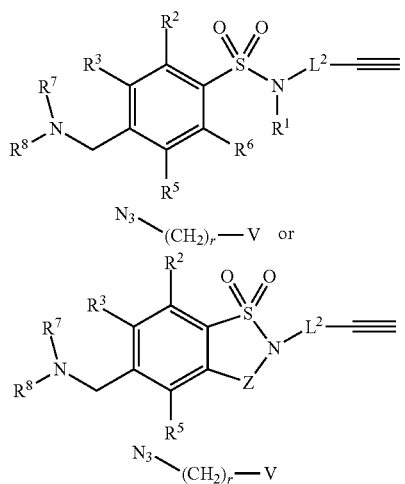

under conditions such that a compound of formula IL or IM is formed.

In certain embodiments, the disclosure relates to methods of making compounds of formula IN or formula IO as reported herein, Formula IN
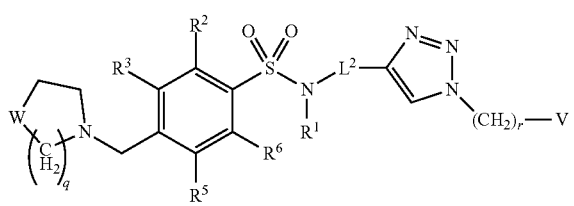

Formula IO
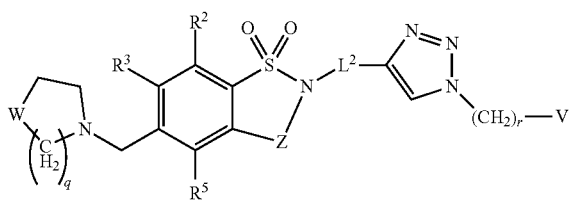

comprising mixing the following alkyne and azide compounds:

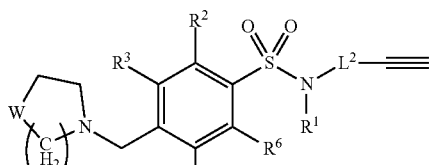

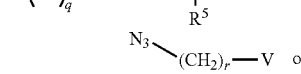

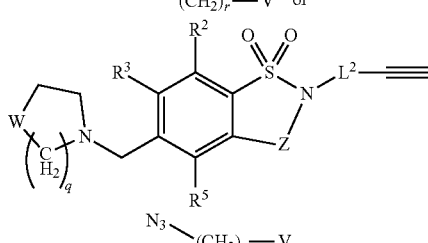

under conditions such that that a compound of formula IN or IO is formed.

Radiohalogenation

In certain embodiments, for any of the formula provided herein V is $^{18}$F. Radiofluorination reactions are typically nucleophilic substitutions. Homoaromatic nucleophilic substitutions with fluoride usually require activated aromatic rings, bearing both a good leaving group (e.g. a halogen, a nitro- or a trimethylammonium group) and a strong electron-withdrawing substituent (e.g. a nitro-, cyano- or acyl group) preferably placed para to the leaving group, whereas aliphatic nucleophilic substitutions typically utilize leaving group (usually a halogen or a sulphonic acid derivative such as mesylate, tosylate, or triflate).

[$^{18}$F] fluoride is produced by irradiation of water (containing H$_2$$^{18}$O) with protons resulting in the reaction $^{18}$O(p, n)$^{18}$F. For production efficiency and radiochemical purity, it is desirable to use water that is as highly enriched as possible. The [$^{18}$F] isotope is then separated from water and processed for production of a radiopharmaceutical agent. Typically fluoride recovery is based on ion exchange resins. The recovery is carried out in two steps (extraction and elution): first the anions (not only fluoride) are separated from the enriched [$^{18}$O] water and trapped on a resin and then, said anions, including [$^{18}$F] fluoride, are eluted into a mixture containing water, organic solvents, a base, also called activating agent or phase transfer agent or phase transfer catalyst, such as for example the complex potassium carbonate-Kryptofix$_{222}$ (K$_2$CO$_3$—K$_{222}$) or a tetrabutylammonium salt. Typical labeling method uses low water content solutions. An evaporation step follows the recovery of the [$^{18}$F]fluoride, e.g., azeotropic evaporation of acetonitrile or other low boiling temperature organic solvent.

Alternatively the extraction process is performed by passing the [$^{18}$F] aqueous solution on a solid support as reported in U.S. Pat. No. 8,641,903. This solid support is typically loaded with a trapping agent, e.g., compound comprising a quaternary amine, which is adsorbed on the solid support and allows the [$^{18}$F] activity to be trapped because of its positive charge. The solid support is then flushed with a gas or a neutral solvent to remove or push out most of the residual water. The [$^{18}$F] is at last eluted in an organic solvent or in a mixture of organic solvents and is immediately usable for the labelling of precursor compounds.

The compounds described herein could also be labeled by radionuclide bromine or iodine through traditional labeling procedures such as tributyltin derivatives. (See, for example, Plisson et al, Synthesis and in vivo evaluation of fluorine-18 and iodine-123 labeled 2beta-carbo(2-fluoroethoxy)-3beta-(4'-((Z)-2 iodoethenyl)phenyl)nortropane as a candidate serotonin transporter imaging agent. J Med Chem, 2007, 50(19):4553-60; Plisson et al, Synthesis, radiosynthesis, and biological evaluation of carbon-11 and iodine-123 labeled 2beta-carbomethoxy-3beta-[4'-((Z)-2-haloethenyl)phenyl] tropanes. J Med Chem, 2004, 47(5):1122-35; Li et al, Synthesis of structurally identical fluorine-18 and iodine isotope labeling compounds for comparative imaging. Bioconjug Chem, 2003, 14(2):287-94; Goodman et al., Synthesis and characterization of iodine-123 labeled 2beta-carbomethoxy-3beta-(4'-((Z)-2-iodoethenyl)phenyl) nortropane. J Med Chem, 2003, 46(6):925-35; Maziere et al, $^{76}$Br-beta-CBT, a PET tracer for investigating dopamine neuronal uptake. Nucl Med Biol, 1995, 22(8):993-7).

Kits

It is contemplated that precursor compounds are labeled with radionuclides using methods reported herein to provide the tracers. These tracers may be prepared at the location of the subject near the time the subject is exposed to a imaging device. Thus, in certain embodiments, the disclosure contemplates kits comprising compounds or precursor compounds (e.g., compounds that react with recently generated $^{18}$F), disclosed herein, e.g., compounds disclosed herein comprising alkyl or alkoxy groups that are terminally substituted with tosylate and mesylate groups; or alkyne and azide compounds disclosed herein and a solid support.

In certain embodiments, the disclosure contemplates a kit comprising compounds disclosed herein or precursor compounds comprising alkyl or alkoxy groups terminally substituted with halogen, hydroxyl, thiol, —O-p-toluenesulfonyl, —O-p-bromobenzenesulfonyl, —O-(2- or 4)-nitrobenzene sulfonyl, —O-methanesulfonyl, —O-trifluoromethanesulfonyl, —O-5(dimethylamino)naphthalene-1-sulfonyl, —S-p-toluenesulfonyl, —S-p-bromobenzenesulfonyl, —S-(2- or 4)-nitrobenzene sulfonyl, —S-methanesulfonyl, —S-trifluoromethanesulfonyl, —S-5(dimethylamino)naphthalene-1-sulfonyl. In certain embodiments, the kit may further comprise a compound disclosed herein having a terminal hydroxy or thiol and an activating agent such as p-toluenesulfonyl chloride, p-bromobenzenesulfonyl chloride, (2- or 4)-nitrobenzene sulfonyl chloride, methanesulfonyl chloride, trifluoromethanesulfonyl chloride, 5 (dimethylamino)naphthalene-1-sulfonyl chloride, dicyclohexylcarbodiimide, bromo-tripyrrolidino-phosphonium hexafluorophosphate, bromotris(dimethylamino) phosphonium hexafluorophosphate, 2-(6-Chloro-1H-benzotriazol-1-yl)-N,N,N',N'-tetramethylaminium hexafluorophosphate, N-[(5-Chloro-1H-benzotriazol-1-yl)-dimethylamino-morpholino]-uronium hexafluorophosphate N-oxide, tetramethylfluoro formamidinium hexa-fluorophosphate, 1-[1-(Cyano-2-ethoxy-2-oxoethylidene-aminooxy)-dimethylamino-morpholino]-uronium hexafluorophosphate, 2-(1-oxy-pyridin-2-yl)-1,1,3,3-tetramethyl-isothiouronium tetrafluoroborate]; or alkyne and azide compounds disclosed herein and a solid support. In certain embodiments, the solid support optionally comprises $^{18}$F salts.

In some embodiments, the solid support is selected from the group of solid phase extraction resins or liquid chromatography resins, e.g., silica (oxide) based or non-silica (metal oxide or polymers) based particles optionally functionalized (e.g., by organosilanization) with alkyl chains for example C4, C8, C18, C18, C30 or other functional groups, e.g., polar groups (amide, carbamate, sulfamide, and ureas) embedded within alkyl chains or branched alkyl groups or polymeric packings. Polymeric column packing refers to particles made by the process of reacting silica surface silanol groups with halogenated di or trifunctional silanes.

In some embodiments, the solid support is selected from the group consisting of solid phase extraction resins and liquid chromatography resins resulting from the copolymerization of divinylbenzene and/or styrene, or by the copolymerization with vinylpyrrolidone, vinylacetate, (methacryloyloxymethyl)naphtalene, 4,4'-bis(maleimido) diphenylmethane, p,p'-dihydroxydiphenylmethane diglycidylmethacrylic ester, p,p'-dihydroxydiphenylpropane diglycidylmethacrylic ester, 2-hydroxyethylmethacrylate (HEMA), 2,2-dimethylaminoethylmethacrylate (DMAEMA), ethylenedimethacrylate glycidylmethacrylate, N-vinylcarbazole, acrylonitrile, vinylpyridine, N-methyl-N-vinylacetamide, aminostyrene, methylacrylate, ethylacrylate, methylmethacrylate, N-vinylcaprolactam, N-methyl-N-vinylacetamide.

In some embodiments, the solid support comprises or is functionalized with or preconditioned with quaternary ammonium salts, e.g., tetraethylammonium carbonate, tetrabutylammonium carbonate or potassium carbonate cryptands such as 1,4,10-Trioxa-7,13-diaza-cyclopentadecane, 4,7,13,16,21,24-Hexaoxa-1,10-diazabicyclo[8.8.8] hexacosane, 4,7,13,16,21-Pentaoxa-1,10-diazabicyclo [8.8.5]tricosane, 4,7,13,18-Tetraoxa-1,10-diazabicyclo [8.5.5]eicosane, 5,6-Benzo-4,7,13,16,21,24-hexaoxa-1,10-diazabicyclo[8.8.8]hexacos-5-ene; the group of glymes including crown ethers such as for example 4'-Aminobenzo-15-crown-5, 4'-Aminobenzo-15-crown-5, 4'-Aminobenzo-15-crown-5 hydrochloride, 4'-Aminobenzo-18-crown-6, 4'-Aminodibenzo-18-crown-6, 2-Aminomethyl-15-crown-5, 2-Aminomethyl-15-crown-5, 2-Aminomethyl-18-crown-6, 4'-Amino-5'-nitrobenzo-15-crown-5, 4'-Amino-5'-nitrobenzo-15-crown-5, 1-Aza-12-crown-4, 1-Aza-15-crown-5, 1-Aza-15-crown-5, 1-Aza-18-crown-6, 1-Aza-18-crown-6, Benzo-12-crown-4, 5,6-Benzo-4,7,13,16,21,24-hexaoxa-1,10-diazabicyclo[8.8.8]hexacos-5-ene, 1-Benzyl-1-aza-12-crown-4, Bis[(benzo-15-crown-5)-15-ylmethyl]pimelate, 4'-Bromobenzo-15-crown-5, 4-tert-Butylbenzo-15-crown-5, 4-tert-Butylcyclohexano-15-crown-5, 4'-Carboxybenzo-15-crown-5, polyethylene glycols (PEG), polyethylene oxides (PEO); the group of calixarenes such as for example 4-tert-Butylcalix[4]arene, 4-tert-Butylcalix[4]arene, 4-tert-Butylcalix[4]arene, 4-tert-Butylcalix[5]arene, 4-tert-Butylcalix[6] arene, 4-tert-Butylcalix[6]arene, 4-tert-Butylcalix[6]arene, 4-tert-Butylcalix[8]arene, 4-tert-Butylcalix[8]arene, 4-tert-Butylcalix[4]arene-tetraacetic acid tetraethyl ester, 4-tert-Butylcalix[4]arenetetraacetic acid tetraethyl ester, 4-tert-Butylcalix[4]arene-tetraacetic acid triethyl ester, Calix[4] arene, Calix[6]arene, Calix[8]arene, 4-(Chloromethyl)calix [4]arene, 4-Isopropylcalix[4]arene, C-Methylcalix[4] resorcinarene, C-Methylcalix[4]resorcinarene, meso-Octamethylcalix(4)pyrrole, 4-Sulfocalix[4]arene, 4-Sulfocalix[4]arene sodium salt, C-Undecylcalix[4]resorcinarene monohydrate, C-Undecylcalix[4]resorcinarene monohydrate, the group of cyclodextrines such as α-Cyclodextrin, β-Cyclodextrin, γ-Cyclodextrin, (2,6-Di-O-)ethyl-3-cyclodextrin, 6-O-α-D-Glucosyl-β-cyclodextrin, Heptakis(6-O-t-butyldimethylsilyl-2,3-di-O-acetyl)-β-cyclodextrin, Heptakis(2,6-di-O-methyl)-3-cyclodextrin, Heptakis(2,3,6-tri-O-acetyl)-3-cyclodextrin, Heptakis(2,3,6-tri-O-benzoyl)-3-cyclodextrin, Hexakis (6-O-tertbutyl-dimethylsilyl)-α-cyclodextrin, Hexakis (2,3,6-tri-O-acetyl)-α-cyclodextrin, Hexakis (2,3,6-tri-O-methyl)-α-cyclodextrin, (2-Hydroxyethyl)-β-cyclodextrin, 6-O-α-Maltosyl-β-cyclodextrin hydrate, Methyl-P-cyclodextrin, 6-Monodeoxy-6-monoamino-β-cyclodextrin, Octakis (6-O-t-butyldimethylsilyl)-γ-cyclodextrin, Sulfopropyl-β-cyclodextrin, Triacetyl-α-cyclodextrin, Triacetyl-β-cyclodextrin; and the group of EDTA and derivatives such as for example Ethylenediamine-N,N'-diacetic acid, 2-Bis(2-aminophenoxy)ethane-N,N,N',N'-tetraacetic acid, trans-1,2-Diaminocyclohexane-N,N,N',N'-tetraacetic acid monohydrate, trans-1,2-Diaminocyclohexane-N,N,N',N'-tetraacetic acid monohydrate, 1,3-Diamino-2-hydroxypropane-N,N,N',N'-tetraacetic acid, 1,2-Diaminopropane-N,N,N',N'-tetraacetic acid, 1,3-Diaminopropane-N,N,N',N'-tetraacetic acid, 1,3-Diamino-2-propanol-N,N,N',N'-tetraacetic acid, Diethylenetriamine-pentaacetic acid calcium trisodium salt hydrate, N-(2-Hydroxyethyl)ethylenediaminetriacetic acid trisodium salt hydrate, N-(2-Hydroxyethyl)ethylenediamine-N,N',N'-triacetic acid.

Imaging Methods

In certain embodiments, the compounds disclosed herein are labeled with a radionuclide suitable for imaging with gamma, PET or SPECT imaging technology, preferably an isotope suitable for PET imaging. In other embodiments, the compounds described herein are labeled with $^{11}$C or $^{13}$C, for example by incorporating into the carbons of the compounds, for MRI or MRS imaging. In other embodiments, the compounds described herein are labeled with a dye, for example a near-infrared dye, suitable for optical imaging. Exemplary compositions described here can be used to image, detect, and/or predict cancer, in particular the spread of cancer, within an organism.

Instruments for detecting and monitoring by radionuclide imaging the location of a tracer in the body of a subject include positron emission tomography (PET) and single photon emission computed tomography (SPECT) scanners. These may be combined with other methods such as computerized tomography (CT) scans and MRI. A CT scan combines a series of X-ray images taken from different angles and uses computer processing to create cross-sectional images, or slices, of the bones, blood vessels and soft tissues inside your body. These scans or associated data can be used to create computerized images that take place in tissue. A scanner records data that a computer constructs into two- or three-dimensional images. In a typical method, radioactive drug is injected into the subject, e.g., a vein, and a scanner is used to make detailed images of areas inside the body where the radioactive material is taken up by the cells, tissue, fluids, or organs. For example, when imaging for lymphoma, the scans can show the uptake of the radionuclides in the lymph nodes, the groin, both axilla (armpit), and neck.

In certain embodiments, the disclosure relates to imaging methods comprising a) administering a compound comprising a radionuclide or positron-emitting radionuclide disclosed herein to a subject; and b) scanning the subject for the emission, positron-emissions or other gamma-emissions. The methods typically further comprise the steps of detecting the emissions and creating an image of an area of the subject indicating or highlighting the location of the compound containing radionuclide in the subject. In certain embodiments, the area of the subject is the lymph nodes, groin, axilla, neck, lungs, liver, kidney, pancreas, stomach, balder, intestines, circulatory system, breast, prostate, gallbladder, or brain.

Alternatively the compounds of the present disclosure may be labeled with one or more radionuclides, such as $^{11}$C, $^{18}$F, $^{76}$Br, $^{123}$I, $^{124}$I, $^{131}$I, $^{13}$N, or $^{15}$O. Radionuclides used in PET scanning are typically positron-emitting isotopes with short half-lives such as carbon-11 (approximately 20 min), nitrogen-13 (approximately 10 min), oxygen-15 (approximately 2 min), and fluorine-18 (approximately 110 min). The compound may be administered by any suitable technique known in the art, such as direct injection. Injection may be intravenous (IV). Administration may be general or local to the site of interest, such as to a tumor. The compound may be used in conjunction with another probe, for example a fluorescent probe capable of visualizing a particular tissue or a tumor. The two (or more) probes may be administered together, separately or sequentially. The imaging compound of the present disclosure may be used to diagnose, assess or monitor the progression or treatment of a disease or condition.

The imaging probe of the present disclosure may be used to investigate the effects of a test compound on CXCR4. For example, the imaging probe may be administered together with a test compound, to and the effect of the test compound be assayed in real time in vivo using a method in accordance with the present disclosure.

The compounds of the disclosure are useful as tumor binding agents and as receptor-binding ligands, and in radioisotopic form are especially useful as tracer compounds for tumor imaging techniques, including PET and SPECT imaging. Particularly useful as an imaging agent are those compounds labeled with F-18 since F-18 has a half-life of 110 minutes, which allows sufficient time for incorporation into a radio-labeled tracer, for purification and for administration into a human or animal subject. In addition, facilities more remote from a cyclotron, up to about a 200 mile, radius can make use of F-18 labeled compounds.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is [$^{123}$I], a γ-emitter with a 13.3 hour half-life. Compounds labeled with [$^{123}$I] can be shipped up to about 1000 miles from the manufacturing site, or the isotope itself can be transported for on-site synthesis.

Accordingly, the compounds of the disclosure can be rapidly and efficiently labeled with [$^{123}$I] for use in SPECT analysis as an alternative to PET imaging. Furthermore, because of the fact that the same compound can be labeled with either isotope, it is possible to compare the results obtained by PET and SPECT using the same tracer.

Other halogen isotopes can serve for PET or SPECT imaging, or for conventional tracer labeling. These include $^{75}$Br, $^{76}$Br, $^{77}$Br and $^{82}$Br as having usable half-lives and emission characteristics. In general, the chemical means exist to substitute any halogen moiety for the described isotopes. Astatine can be substituted for other halogen isotopes, [$^{210}$At] emits alpha particles with a half-life of 8.3 h. At-substituted compounds are therefore useful for tumor therapy where binding is sufficiently tumor-specific.

In certain embodiments, the disclosure provides methods for tumor imaging using PET and SPECT. The methods entail administering to a subject (which can be human or animal, for experimental and/or diagnostic purposes) an image-generating amount of a compound of the disclosure, labeled with the appropriate isotope and then measuring the distribution of the compound by PET if [$^{18}$F] or other positron emitter is employed, or SPECT if [$^{123}$I] or other gamma emitter is employed. An image-generating amount is that amount which is at least able to provide an image in a PET or SPECT scanner, taking into account the detection sensitivity and noise level of the scanner, the age of the isotope, the body size of the subject and route of administration.

It will be understood that compounds of the disclosure can be labeled with an isotope of any atom or combination of atoms in the structure. While [$^{18}$F], [$^{123}$I] and have been emphasized herein as being particularly useful for PET, SPECT and tracer analysis, other uses are contemplated including those flowing from physiological or pharmacological properties of stable isotope homologs and will be apparent to those skilled in the art.

In certain embodiments, the compositions disclosed herein are used for imaging to study CXCR4 related conditions. CXCR4 is a receptor that malignant tumor cells express. Using CXCR4 as a target to image cancer has been reported. However, improvements in stability and blood clearance are needed. Positron Emission Tomography (PET) involves detection of pairs of gamma rays emitted indirectly by a positron-emitting radionuclide (tracer), which is introduced into the body on a biologically active molecule. Images of tracer concentration in the body are then reconstructed by computer analysis. Current PET imaging agents used in clinical oncology either lack specificity for the cancer, are not accurate predictors of metastasis, or are eliminated too quickly or too slowly from the body for optimal imaging.

Methods of use of the imaging agents provided herein include, but are not limited to: methods of imaging tissue; methods of imaging precancerous tissue, cancer, and tumors; methods of treating precancerous tissue, cancer, and tumors; methods of diagnosing precancerous tissue, cancer, and tumors; methods of monitoring the progress of precancerous tissue, cancer, and tumors; methods of imaging abnormal tissue, and the like. The methods can be used to detect, study, monitor, evaluate, and/or screen, biological events in vivo or in vitro, such as, but not limited to, CXCR4 related biological events.

The imaging agents, compositions, and methods of use provided can be used in vivo or in vitro for imaging cancer cells or tissue; imaging precancerous cells or tissue; diagnosing precancerous tissue, cancer, tumors, and tumor metastases; monitoring the progress and/or staging of precancerous tissue, cancer, and tumors; methods of predicting tumor metastasis; methods of evaluating drug effectiveness on treating and/or preventing cancer, tumors, metastasis, and the like.

In diagnosing and/or monitoring the presence of cancerous cells, precancerous cells, and tumors in a subject, labeled compounds are administered to the subject in an amount effective to result in uptake of the labeled compound into the cells or binding to the labeled compound. After administration of the labeled compounds, cells that take up or bind with the labeled compound are detected using PET or SPECT imaging. Embodiments of the present disclosure can non-invasively image tissue throughout an animal or patient.

It should be noted that the amount effective to result in uptake of the compound into the cells or tissue of interest will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Preferred imaging methods provided by the present disclosure include the use of the radionuclide containing compounds of the present disclosure and/or salts thereof that are capable of generating at least a 2:1 target to background ratio of radiation intensity, or more preferably about a 5:1, about a 10:1 or about a 15:1 ratio of radiation intensity between target and background. In certain preferred methods, the radiation intensity of the target tissue is more intense than that of the background. In other embodiments, the present disclosure provides methods where the radiation intensity of the target tissue is less intense than that of the background. Generally, any difference in radiation intensity between the target tissue and the background that is sufficient to allow for identification and visualization of the target tissue is sufficient for use in the methods of the present disclosure.

In preferred methods of the present disclosure, the compounds of the present disclosure are excreted from tissues of the body quickly to prevent prolonged exposure to the radiation of the radiolabeled compound administered to the patient. In particular embodiment, the radionuclide labeled compounds provided herein can be used on an outpatient basis. Typically compounds of the present disclosure are eliminated from the body in less than about 24 hours. More preferably, compounds of the present disclosure are eliminated from the body in less than about 16 hours, 12 hours, 8 hours, 6 hours, 4 hours, 2 hours, 90 minutes, or 60 minutes.

Preferred imaging agents are stable in vivo such that substantially all, e.g., more than about 50%, 60%, 70%, 80%, or more preferably 90% of the injected compound is not metabolized by the body prior to excretion.

Typical subjects to which compounds of the present disclosure may be administered will be mammals, particularly primates, especially humans. For veterinary applications, a wide variety of subjects will be suitable, e.g. livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine or tissue samples, or blood urine or tissue samples of the animals mentioned for veterinary applications.

Images can be generated by virtue of differences in the spatial distribution of the imaging agents that accumulate at a site having expression, and/or overexpression, of the CXCR4 receptors. The spatial distribution may be measured using any imaging apparatus suitable for the particular label, for example, a gamma camera, a PET apparatus, a SPECT apparatus, MRS, MRI or optical imaging apparatus, and the like. The extent of accumulation of the imaging agent may be quantified using known methods for quantifying radioactive emissions. A particularly useful imaging approach employs more than one imaging agent to perform simultaneous studies. Alternatively, the imaging method may be carried out a plurality of times with increasing administered dose of the pharmaceutically acceptable imaging composition of the present disclosure to perform successive studies using the split-dose image subtraction method, as are known to those of skill in the art.

Preferably, an amount of the imaging agent effective for detection is administered to a subject. An effective amount of the imaging agent may be administered in more than one injection. The effective amount of the imaging agent can vary according to factors such as the degree of susceptibility of the individual, the age, sex, and weight of the individual, idiosyncratic responses of the individual, the dosimetry, and the like. Effective amounts of the imaging agent can also vary according to instrument and film-related factors. Optimization of such factors is well within the level of skill in the art.

The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

In one embodiment, a method of imaging metastases of a malignant cell is provided that includes administering a compound disclosed herein to a subject. The malignant cell can be a tumor cell. In certain embodiments, the compound can be provided to a host before treatment of a tumor. In a separate embodiment, the compound is provided to a patient that has been treated for cancer to reduce the likelihood of recurrence, or reduce mortality associated with a particular tumor. In another embodiment, the compound is administered to a host at high risk of suffering from a proliferative disease. Such high risk can be based, for example, on family history or on a history of exposure to known or presumed carcinogens.

Subjects, including humans suffering from, or at risk for, a proliferative disorder can be treated by administering an effective amount of the imaging agent or a pharmaceutically acceptable prodrug or salt thereof in the presence of a pharmaceutically acceptable carrier or diluent. The imaging agent or composition comprising the imaging agent can be administered by any appropriate route, for example, orally, parenterally, intravenously, intradermally, subcutaneously, or topically, in liquid or solid form.

A preferred dose of the compound will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent compound to be delivered. If the salt, ester or prodrug exhibits activity in itself, the effective dosage can be estimated as above using the weight of the salt, ester or prodrug, or by other means known to those skilled in the art.

In a separate embodiment, a method of imaging or detecting proliferative disorders by administering a compound disclosed herein to a subject is provided. In certain embodiments, the proliferative disorder is cancer, and in particular, the disorder is a metastatic cancer. The compounds of the disclosure can be administered to a host suffering from or at risk of suffering from metastasis of a proliferative disorder, such as cancer. In particular embodiments, the cancer is breast cancer, brain tumor, pancreatic cancer, ovarian tumor, particularly an ovarian epithelial tumor, prostate cancer, kidney cancer, or non-small cell lung cancer Therapeutic Applications In certain embodiments, the compounds described herein are useful for imaging. The compounds or derivatives can be used to treat disorders of abnormal cell proliferation generally, examples of which include, but are not limited to, types of cancers and proliferative disorders listed below. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, Int. J. Dermatol. 18:111, 1979). Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. Nature, 1993, 362:801-809). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic microangiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr. (1990) The New England Journal of Medicine, 322:1277-1289), and to be caused by auto-antibodies produced against collagen and IgE.

In certain embodiments, the disclosure relates to methods of treating or preventing rheumatoid arthritis or psoriatic arthritis comprising administering pharmaceutical composition comprising a compound as described herein to a subject in need thereof.

In certain embodiments, the disclosure relates to methods of treating or preventing arthritis comprising administering pharmaceutical composition comprising a compound as described herein in combination with another active ingredient to a subject in need thereof.

In certain embodiments, the other active agent is a non-steroidal anti-inflammatory drugs (NSAIDs), ibuprofen, acetaminophen, methotrexate, abatacept, adalimumab, azathioprine, ciclosporin, rituximab, chloroquine, hydroxychloroquine, etanercept, golimumab, infliximab, leflunomide, minocycline, or combinations thereof.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Examples of cancers or proliferative disorders which can be the primary tumor that is treated include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

In certain embodiments, the subject is diagnosed with acute childhood lymphoblastic leukemia; acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignancies, anal cancer, astrocytoma, bile duct cancer, bladder cancer, bone cancer, brain stem glioma, brain tumors, breast cancer, cancer of the renal pelvis and ureter, central nervous system (primary) lymphoma, central nervous system lymphoma, cerebellar astrocytoma, cerebral astrocytoma, cervical cancer, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood cerebral astrocytoma, childhood extracranial germ cell tumors, childhood Hodgkin's disease, childhood Hodgkin's lymphoma, childhood hypothalanic and visual pathway glioma, childhood lymphoblastic leukemia, childhood medulloblastoma, childhood non-Hodgkin's lymphoma, childhood pineal and supratentorial primitive neuroectodermal tumors, childhood primary liver cancer, childhood rhabdomyosarcoma, childhood soft tissue sarcoma, childhood visual pathway and hypothalamic glioma, chronic lymphocytic leukemia, chronic myelogenous leukemia, colon cancer, cutaneous T-cell lymphoma, endocrine pancreas islet cell carcinoma, endometrial cancer, ependymoma, epithelial cancer, esophageal cancer, Ewing's sarcoma and related tumors, exocrine pancreatic cancer, extracranial germ cell tumor, extragonadal germ cell tumor, extrahepatie bile duct cancer, eye cancer, female Breast cancer, Gaucher's disease, gallbladder cancer, gastric cancer, gastrointestinal carcinoid tumor, gastrointestinal tumors, germ cell tumors, gestational trophoblastic tumor, hairy cell leukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, kidney cancer, laryngeal cancer, lip and oral cavity cancer, liver cancer, lung cancer, lympho proliferative disorders, macroglobulinemia, male breast cancer, malignant mesothelioma, malignant thymoma, medulloblastomia, melanoma, mesothelioma, metastatie occult primary squamous neck cancer, metastatie primary squamous neck cancer, metastatie squamous neck cancer, multiple myeloma, multiple myeloma/plasma cell neoplasm, myelodysplasia syndrome, myelogenous leukemia, myeloid leukemia, myeloproliferative disorders, nasal cavity and paranasal sinus cancer, nasopharyngeal cancer, neuroblastoma, non-Hodgkin's lymphoma during pregnancy, nonmelanoma skin cancer, non-small cell lung cancer, occult primary metastatie squamous neck cancer, oropharyngeal cancer, osteo/malignant fibrous sarcoma, osteosarcoma/malignant fibrous histiocytoma, osteosarcoma/malignant fibrous histiocytoma of bone, ovarian epithelial cancer, ovarian germ cell tumor, ovarian low malignant potential tumor, pancreatic cancer, paraproteinemias, purpura, parathyroid, cancer, penile cancer, pheochromocytoma, pituitary tumor, plasma cell neoplasm/multiple myeloma, primary central nervous system lymphoma, primary liver cancer, prostate cancer, rectal cancer, renal cell cancer, renal pelvis and ureter cancer, retinoblastoma, rhabdomyosarcoma, salivary gland cancer, sarcoidosis sarcomas, sezary syndrome, skin cancer, small cell lung cancer, small Intestine cancer, soft tissue sarcoma, squamous neck cancer, stomach cancer, supratentorial primitive neuroectodermal and pineal tumors, T-cell lymphoma, testicular cancer, thymoma, thyroid cancer, transitional cell cancer of the renal pelvis and ureter, transitional renal pelvis and ureter cancer, trophoblastic tumors, ureter and renal pelvis cell cancer, urethial cancer, uterine cancer, uterine sarcoma, vaginal cancer, visual pathway and hypothalamic glioma, vulvar cancer, Waldenstrom's macroglobulinemia, Wilm's tumor, and any other hyperproliferative disease located in an organ system listed above.

In certain embodiments, the compound derivatives disclosed herein can be used to treat or prevent hyperplastic disorders including, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia; leukemia (including acute leukemia (e.g., acute lymphocytic leukemia, acute myelocytic leukemia (including myeloblasts, promyelocyte, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and, carcinomas such as fibrosarcoma, myxosarcoma, fiposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

In a separate embodiment, the disclosure relates to a method for the treatment of, prevention of, or reduced severity of, age-related macular degeneration (ARMD) and other pathogenic states involving macular retinal pigment epithelial (RPE) cells by administering at least one compound or derivative described herein to a subject in need thereof.

CXCR4 plays a role in ocular diseases involving the retina such as age-related macular degeneration (ARMD). The retinal pigment epithelium has a major role in the physiological renewal of photoreceptor outer segments in the provision of a transport and storage system for nutrients essential to the photoreceptor layer. The retinal pigment epithelial (RPE) cells predominantly express CXCR4 receptors. (Crane, et al. (2000) J. Immunol. 165: 4372-4278). CXCR4 receptor expression on human retinal pigment epithelial cells from the blood-retina barrier leads to chemokine secretion and migration in response to stromal cell-derived factor Ia. J. Immunol. 200; 165: 4372-4278). The level of CXCR4 mRNA expression increases upon stimulation with IL-1β or TNFα (Dwinell, et al. (1999) Gastroenterology. 117: 359-367). RPE cells also migrated in response to SDF-1α indicating that SDF-1α/CXCR4 interactions may modulate the effects of chronic inflammation and subretinal neovascularization at the RPE site of the blood-retina barrier. (Crane IJ, Wallace C A, McKillop-Smith S, Forrester J V. CXCR4 receptor expression on human retinal pigment epithelial cells from the blood-retina barrier leads to chemokine secretion and migration in response to stromal cell-derived factor Ia. J. Immunol. 200; 165: 4372-4278).

Age-related macular degeneration is characterized by both primary and secondary damage of macular RPE cells. Early stages of ARMD are characterized by macular drusen, and irregular proliferation and atrophy of the RPE. The late stages of ARMD present with geographic RPE atrophy, RPE detachment and rupture, choroidal neovascularaization and fibrovascular disciform scarring. Common first symptoms include metamorphopisia and/or general central vision loss resulting in reading disability and difficulties in detecting faces. Late stages of ARMD cause central scomota, which is extremely disabling if occurrence is bilateral (Bressler and Bressler (1995) Ophthalmology. 1995; 102: 1206-1211).

In a separate embodiment, a method for the treatment of, prevention of, or reduced severity of inflammatory disease states, neovascularization, and wound healing including administering at least one compound or derivative described herein to a subject in need thereof. Vascular endothelial cells express a multitude of chemokine receptors, with CXCR4 being particularly prominent (Gupta, et al, J Biol Chem, 1998, 273: 4282; Volin et al, Biochem Biophys Res Commnun, 1998, 242:46).

A RT-PCR based strategy which utilized CXCR4 specific primers demonstrated that mRNA for the chemokine receptor CXCR4 is expressed not only in primary cultures and transformed type II alveolar epithelial cells (pneumocytes) but also in a number of epithelial cell lines derived from various other tissues (Murdoch et al, Immunology, 1998, 98(1):36-41). Unlike with endothelial cells, CXCR4 is the only chemokine receptor expressed on epithelial cells. The receptor may have a functional role in epithelial pathology. CXCR4 expressed on the epithelium may facilitate the recruitment of phagocytic cells to sites of inflammation by direct effects on epithelial cells. CXCR4 may also have other functional roles within the immune response or participate in wound healing or neovascularization. CXCR4 may also be involved in the pathophysiology of several acute or chronic inflammatory disease states associated with the epithelium.

Certain inflammatory chemokines can be induced during an immune response to promote cells of the immune system to a site of infection. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. Responses to chemokines include increasing or decreasing expression of membrane proteins, proliferation, and secretion of effector molecules.

In a particular embodiment, the compounds of the disclosure can be administered to a host at risk of, or suffering from, an inflammatory condition. In one embodiment, the compounds are administered for the treatment or prophylaxis of an inflammatory disorder. In certain embodiments, the inflammatory disorder or condition is mediated by chemokines.

Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barre, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells).

In one embodiment, compounds, compositions and methods of treatment of respiratory disorders comprising administering a compound as described herein to a subject in need thereof. Respiratory disorders that may be prevented or treated include a disease or disorder of the respiratory system that can affect any part of the respiratory tract. Respiratory disorders include, but are not limited to, a cold virus, bronchitis, pneumonia, tuberculosis, irritation of the lung tissue, hay fever and other respiratory allergies, asthma, bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis. Other respiratory disorders include allergic and non-allergic rhinitis as well as non-malignant proliferative and/or inflammatory disease of the airway passages and lungs. Non-malignant proliferative and/or inflammatory diseases of the airway passages or lungs means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In one embodiment, the compounds or derivatives of the disclosure are administered to a patient suffering from a cardiovascular disorder related to inflammation. Cardiovascular inflammatory disorders include atherosclerosis, post-angioplasty, restenosis, coronary artery diseases, angina, and other cardiovascular diseases.

In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes.

In addition, the disclosure is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the disclosure is directed to methods of treating animal subjects, in particular, veterinary and human patients, who are defective in white blood cell (WBC 8 count), or who would benefit from elevation of WBC levels using the compounds disclosed herein. Moreover, the disclosure is directed to methods of effecting regeneration of cardiac tissue in a subject in need of such regeneration using the disclosed compounds.

The compounds or derivatives of the disclosure may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round disclosure thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the disclosure targets a broad spectrum of conditions characterized by a deficiency in white blood cell count, or which would benefit from elevation of said WBC count.

Combination Therapies

In certain embodiments, the disclosure relates to pharmaceutical compositions comprising compounds and derivatives disclosed herein with another active ingredient.

In certain embodiments, the disclosure relates to administering compounds or derivatives disclosed herein in combination with natural ligands CXCR4.

In certain embodiments, compounds disclosed herein can be used in combination with anti-inflammatory agents such as non-steroidal anti-inflammatory drugs (NSAIDs), ibuprofen, naproxen, and acetaminophen. Other contemplated anti-inflammatory agents include acetylsalicylic acid, dolobid, disalcid, dexibuprofen, fenoprofen, ketoprofen, dexketoprofen, flurbiprofen, oxaprozin, loxoprofen, tolmetin, sulindac, etodolac, ketorolac, diclofenac, aceclofenac, nabumetone, piroxicam, meloxicam, tenoxicam, droxicam, lornoxicam, isoxicam, mefenamic acid, meclofenamic acid, flufenamic acid, tolfenamic acid, or combinations thereof.

The cancer treatment may be applied as a sole therapy or may involve, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (Abl) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-ras antisense; and (viii) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se.

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778; 6,369,086; 6,369,087; and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more compounds. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compounds can be administered in the same dosage form or in separate dosage forms with one or more other active agents.

The additional active agent(s) can be formulated for immediate release, controlled release, or combinations thereof.

Pharmaceutical compositions of the compounds of this application, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride or sodium citrate, may also be added.

Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. Such a liquid formulation may be administered directly or filled into a soft gelatin capsule.

The pharmaceutical compositions of the application may be in the form of a sterile injectable preparation. Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

EXAMPLES

Compound Synthesis

The preparation of certain compounds of this disclosure are provided for in FIGS. 7A, 7B, 8, 9, 10.

Synthesis of Compound A. To a solution of 4-(bromomethyl)benzene-1-sulfonyl chloride (1 eqv.) in DCM was added N-methylpropargylamine (1.1 eqv.) under cooling. The reaction mixture was allowed to stir at 0° C. for 6 hr. Reaction was monitored by TLC. After completion of the reaction, the mixture was purified by flash $SiO_2$ column chromatography, eluting with Ethyl acetate-Hexane (1:3, v/v). $^1$H NMR (400 MHz, $CD_3Cl$): δ 7.80 (2H, m), 7.55 (2H, m), 4.51 (2H, s), 4.05 (2H, d, $J_{13}$=2.4 MHz), 2.86 (3H, s), 2.06 (1H, t, $J_{13}$=2.4 MHz) ppm. The purified compound was dissolved in acetonitrile and morpholine (1.1 eqv.) was added. The reaction mixture was allowed to stir at room temperature overnight. After the completion of the reaction, the mixture was filtered through celite and organic solvent was removed by rotary evaporation. The residue was dissolved in DCM and washed with water, brine, and dried over $MgSO_4$ and concentrated. The crude product was purified by flash $SiO_2$ column chromatography, eluting with DCM-Methanol (10:3, v/v). $^1$H NMR (400 MHz, $CD_3Cl$): δ 7.80 (2H, m), 7.60 (2H, m), 4.05 (2H, d, $J_{13}$=2.4 MHz), 3.82 (4H, m), 3.73 (2H, s), 2.85 (3H, s), 2.62 (4H, m), 2.07 (1H, t, $J_{13}$=2.4 MHz) ppm.

Synthesis of Compound B. Compound B was synthesized as described (Tetrahedron Letters 48 (2007) 3953-3957). Briefly, to a suspension of 4-bromophenol (5.00 g, 28.90 mmol) and $K_2CO_3$ (5.99 g, 43.35 mmol) in DMF (100 mL) was added 3-bromo-1-propanol (6.02 g, 43.35 mmol), and the reaction mixture was heated to 70° C. After 12 h, the reaction mixture was cooled to room temperature, quenched with water and aqueous $NH_4Cl$. The organic compound were extracted with Ethyl acetate (3×100 mL). The combined organic layer was washed with brine (3×100 mL), dried over $Na_2SO_4$, and then concentrated under reduced pressure. The residue was purified by flash column chromatography (20% Ethyl acetate/Hexane) to give 3-(4-bromophenoxy)propan-1-ol. $^1$H NMR (400 MHz, $CD_3Cl$): δ 7.35 (2H, d), 6.76 (2H, d), 4.04 (2H, t), 3.81 (2H, t), 2.24 (1H, br), 2.06-1.94 (2H, m) ppm.

The purified 3-(4-bromophenoxy)propan-1-ol (1.00 g, 4.33 mmol), sodium azide (563 mg, 8.66 mmol), sodium ascorbate (44 mg, 0.22 mmol), copper iodide (82 mg, 0.43 mmol), and N, N'-dimethylehtylene amine (DMEDA, 70 μL, 0.65 mmol) were placed in a two-necked round bottom flask equipped with a reflux condenser, and 13 mL of Ethanol-water (7:3) was added under $N_2$ atmosphere. The reaction mixture was stirred at 90° C. for 45 min., and then the reaction mixture was cooled to room temperature, quenched with water, and organic compounds were extracted with Ethyl acetate (3×100 mL). The combined organic layer was washed with brine (3×100 mL), dried over $MgSO_4$ and concentrated under reduced pressure. The residue was purified by flash chromatography (40% Ethyl acetate/Hexane) to afford compound B. $^1$H NMR (400 MHz, $CD_3Cl$): δ 6.95~6.84 (4H, m), 4.06 (2H, t), 3.82 (2H, t), 2.35 (1H, br), 2.07~1.95 (2H, m) ppm.

Synthesis of Compound I. To a mixture of compound A (308 mg, 1.36 mmol) and B (193 mg, 1.36 mmol) in THF (10 mL) was added aqueous solution of 1 M CuSO4 1 mL and 1 M sodium ascorbate 1 mL. The mixture was stirred in $N_2$ atmosphere for 3 h. The reaction mixture was extracted with Ethyl acetate (3×50 mL) and purified by flash chromatography (10% DCM/Methanol). $^1$H NMR (400 MHz, $CD_3Cl$): δ 7.94 (1H, s), 7.89 (2H, m), 7.60~50 (2H, m), 7.53~7.50 (2H, m), 7.06~7.02 (2H, m), 4.47 (2H, t), 4.40 (2H, s), 4.19 (2H, t), 3.78 (4H, br), 3.53 (2H, s), 3.25 (2H, s), 2.88 (3H, s), 2.44 (4H, br), 2.26 (2H, dd) ppm.

Synthesis of Compound C. To a solution of 3-(4-azidophenoxy)-propan-1-ol (498 mg, 2.58 mmol) and trimethylamine (432 μL, 3.09 mmol) in DCM (10 mL) was added slowly methylsulfonyl chloride (1.2 eqv.) in DCM at 0° C. over 10 min. After 30 min, the reaction was quenched with water and aqueous $NH_4Cl$, and organic compound was extracted with DCM (3×100 mL). The combined organic layer was dried over Na$_2$SO$_4$ and then concentrated under reduced pressure. The residue was purified by flash column chromatography (20% EA/Hexane) to afford 3-(4-azidophenoxy) propyl methylsulfonate. $^1$H NMR (400 MHz, CD$_3$Cl): δ 6.95~6.84 (4H, m), 4.42 (2H, t), 4.06 (2H, t), 2.98 (3H, s), 2.20 (2H, dd) ppm.

Synthesis of Compound D. To a mixture of compound A (50 mg, 0.162 mmol) and B (34 mg, 1.1 eqv.) in THF 2 mL was added aqueous solution of 1 M CuSO$_4$ 100 μL and 1 M sodium ascorbate 100 μL. The mixture was stirred at room temperature for 3 h. The reaction mixture was extracted with Ethyl acetate (3×50 mL) and purified by flash chromatography (10% DCM/Methanol).

Or to a solution of compound I (100 mg, 0.199 mmol) and trimethylamine (1.2 eqv.) and 4-dimethylaminopyridine (DMAP, 0.1 eqv) in DCM (10 mL) was added slowly methylsulfonyl chloride (1.2 eqv.) at 0° C. over 10 min. After 30 min stirring, the reaction was quenched with water and aqueous NH$_4$Cl. The compound was extracted with Ethyl acetate and dried over MgSO$_4$, and then concentrated under reduced pressure. The residue was purified by flash column chromatography (10% DCM/Methanol). $^1$H NMR (400 MHz, CD$_3$Cl): δ 7.94 (1H, s), 7.77~7.75 (2H, m), 7.64~59 (2H, m), 7.53~7.50 (2H, m), 7.02~7.01 (2H, m), 4.46 (2H, t), 4.39 (2H, s), 4.13 (2H, t), 3.71 (4H, br), 3.53 (2H, s), 3.55 (2H, s), 3.00 (3H, s), 2.78 (3H, s), 2.44 (4H, br), 2.26 (2H, dd) ppm.). HRMS (ESI-TOF) m/z: [M+H]$^+$ Calcd for C$_{25}$H$_{33}$N$_5$O$_7$S$_2$ 580.18; Found 580.19. Anal. Calcd for C$_{25}$H$_{33}$N$_5$O$_7$S$_2$: C, 51.80; H, 5.74; N, 12.08; S, 11.06; F, 3. Found: C, 51.64; H, 5.67; N, 11.99; S, 10.91.

Synthesis of Compound J. To a solution of 3-(4-azidophenoxy)-propan-1-ol (498 mg, 2.58 mmol) in DCM was added Diethylaminosulfur trifluoride (DAST, 1.8 eqv.) at 0° C. and the resulting mixture was slowly warmed to room temperature and stirred for 14 h. The reaction was cafully quenched with sat. NaHCO$_3$ (aq) and extracted with DCM (×2). The combined organic layers were washed with 0.5 N HCl solution and dried over MgSO$_4$. The extracts was concentrated under reduced pressure, the resulting residue was purified by flash column chromatography (10% EA/Hexane) to afford compound J. $^1$H NMR (300 MHz, CD$_3$Cl): δ 6.97~6.87 (4H, m), 4.73 (1H, t), 4.57 (1H, t), 4.07 (2H, t), 2.23-2.10 (2H, m) ppm. $^{19}$F NMR (300 MHz, CD$_3$Cl): δ 7.81 (1F, m).

Synthesis of Compound K. To a mixture of compound A (50 mg, 0.162 mmol) and J (34 mg, 1.1 eqv.) in THF 2 mL was added aqueous solution of 1 M CuSO$_4$ 100 μL and 1 M sodium ascorbate 100 μL. The mixture was stirred at room temperature for 3 h. The reaction mixture was extracted with Ethyl acetate (3×50 mL) and purified by flash chromatography (10% DCM/Methanol). $^1$H NMR (400 MHz, CD$_3$Cl): δ 7.95 (1H, s), 7.80~7.77 (2H, m), 7.62~7.58 (4H, m), 7.04~7.02 (2H, m), 4.75 (1H, t), 4.59 (1H, t), 4.41 (2H, s), 4.16 (2H, s), 3.75~3.60 (6H, br), 2.80 (3H, s), 2.48 (4H, br), 2.27-2.14 (2H, m) ppm. $^{19}$F NMR (400 MHz, CD$_3$Cl): δ 7.53 (1F, m). HRMS (ESI-TOF) m/z: [M+H]$^+$ Calcd for C$_{24}$H$_{30}$FN$_5$O$_4$S 504.20; Found 504.21. Anal. Calcd for C$_{24}$H$_{30}$FN$_5$O$_4$S: C, 57.24; H, 6.00; N, 13.91; S, 6.37; F, 3.77. Found: C, 57.07; H, 5.88; N, 13.99; S, 6.46; F, 3.67.

Synthesis of Compound E. To a solution of 3-(4-azidophenoxy)-propan-1-ol (498 mg, 2.58 mmol) and trimethylamine (432 μL, 3.09 mmol) in DCM (10 mL) was added slowly toluenesulfonyl chloride (589 mg, 3.09 mmol) in DCM at 0° C. over 10 min. After 30 min, the reaction was quenched with water and aqueous NH$_4$Cl, and organic compound was extracted with DCM (3×100 mL). The combined organic layer was dried over Na$_2$SO$_4$ and then concentrated under reduced pressure. The residue was purified by flash column chromatography (20% EA/Hexane) to afford 3-(4-azidophenoxy) propyl tolunesulfonate. $^1$H NMR (400 MHz, CD$_3$Cl): δ 7.75 (2H, m), 7.25 (2H, m), 6.90 (2H, m), 6.72 (2H, m), 4.23 (2H, t), 3.90 (2H, t), 2.37 (3H, s), 2.09 (2H, dd) ppm.

Synthesis of Compound F. To a solution of compound A (50 mg, 0.162 mmol) and B (56.3 mg, 1.0 eqv.) in THF 2 mL was added aqueous solution of 1 M CuSO$_4$ 100 μL and 1 M sodium ascorbate 100 μL. The mixture was stirred at room temperature for 3 h. The reaction mixture was extracted with Ethyl acetate (3×50 mL) and purified by flash chromatography (5% EA/Hexane).

Or to a solution of compound I (100 mg, 0.199 mmol) and trimethylamine (1.2 eqv.) and 4-Dimethylaminopyridine (DMAP, 0.1 eqv) in DCM (10 mL) was added slowly toluenesulfonyl chloride (1.2 eqv.) at 0° C. over 10 min. After 30 min stirring, the reaction was quenched with water and aqueous NH$_4$Cl. The compound was extracted with Ethyl acetate and dried over MgSO$_4$, and then concentrated under reduced pressure. The residue was purified by flash column chromatography (10% DCM/Methanol.). $^1$H NMR (400 MHz, CD$_3$Cl): δ 7.95 (1H, s), 7.78~7.75 (4H, m), 7.74~7.51 (2H+2H, m), 7.26~7.24 (2H, m), 6.89~6.86 (2H, m), 4.39 (2H, s), 4.25 (2H, t), 4.00 (2H, t), 4.16 (2H, s), 3.70 (4H, br), 3.55 (2H, s), 2.78 (3H, s), 2.44 (4H, br), 2.37 (3H, s), 2.14 (2H, m) ppm. HRMS (ESI-TOF) m/z: [M+H]$^+$ Calcd for C$_{31}$H$_{37}$N$_5$O$_7$S$_2$ 656.21; Found 656.22. Anal. Calcd for C$_{31}$H$_{37}$N$_5$O$_7$S$_2$: C, 56.78; H, 5.69; N, 10.68; S, 9.78. Found: C, 56.48; H, 5.59; N, 10.48; S, 9.80.

Synthesis of Compound G. To a solution of 3-(4-azidophenoxy)-propan-1-ol (506 mg, 2.62 mmol) and trimethylamine (432 μL, 3.09 mmol), and 4-Dimethylaminopyridine (DMAP, 31.4 mg, 0.1 eqv) in DCM (10 mL) was added slowly 4-nitrobenzenesulfonyl chloride (697 mg, 3.09 mmol) in DCM at 0° C. over 10 min. After 30 min, the reaction was quenched with water and aqueous NH$_4$Cl, and organic compound was extracted with DCM (3×100 mL). The combined organic layer was dried over Na$_2$SO$_4$ and then concentrated under reduced pressure. The residue was purified by flash column chromatography (20% EA/Hexane) to afford 3-(4-azidophenoxy) propyl nitrobenzenesulfonate. $^1$H NMR (400 MHz, CD$_3$Cl): δ 8.23~8.20 (2H, m), 8.03~8.01 (2H, m), 6.88~6.85 (2H, m), 6.67~6.64 (2H, m), 4.43 (2H, t), 3.86 (2H, t), 2.13 (2H, dd).

Synthesis of Compound H. To a solution of compound A (50 mg, 0.162 mmol) and B (56.3 mg, 1.0 eqv.) in THF 2 mL was added aqueous solution of 1 M CuSO$_4$ 100 μL and 1 M sodium ascorbate 100 μL. The mixture was stirred at room temperature for 3 h. The reaction mixture was extracted with Ethyl acetate (3×50 mL) and purified by flash chromatography (5% EA/Hexane).

Or to a solution of compound I (100 mg, 0.199 mmol) and trimethylamine (1.2 eqv.) and 4-Dimethylaminopyridine (DMAP, 0.1 eqv) in DCM (10 mL) was added slowly 4-nitrobenzenesulfonyl chloride (1.2 eqv.) at 0° C. over 10 min. After 30 min stirring, the reaction was quenched with water and aqueous NH$_4$Cl. The compound was extracted with Ethyl acetate and dried over MgSO$_4$, and then concentrated under reduced pressure. The residue was purified by flash column chromatography (10% DCM/Methanol). $^1$H NMR (400 MHz, CD$_3$Cl): δ 7.95 (1H, s), 7.78~7.75 (4H, m), 7.74~7.51 (2H+2H, m), 7.26~7.24 (2H, m), 6.89~6.86 (2H, m), 4.39 (2H, s), 4.25 (2H, t), 4.00 (2H, t), 4.16 (2H, s), 3.70 (4H, br), 3.55 (2H, s), 2.78 (3H, s), 2.44 (4H, br), 2.37 (3H, s), 2.14 (2H, m) ppm. HRMS (ESI-TOF) m/z: [M+H]$^+$ Calcd for $C_{30}H_{34}N_6O_9S_2$ 686.18; Found 686.19. Anal. Calcd for $C_{30}H_{34}N_6O_9S_2$: C, 52.47; H, 4.99; N, 12.24; S, 9.34. Found: C, 52.17; H, 5.00; N, 12.00; S, 9.41.

Synthesis of Compound A'. Compound A' was synthesized in the same procedure as 'compound A' except using N-propargylamine instead of N-methylpropargylamine. $^1$H NMR (400 MHz, $CD_3Cl$): δ 7.80 (2H, m), 7.47 (2H, m), 4.86 (2H, s), 3.82 (2H, d, $J_{13}$=2.4 MHz), 3.70 (4H, m), 3.54 (1H, s), 2.42 (4H, m), 2.06 (1H, t, $J_{13}$=2.4 MHz) ppm.

Synthesis of Compound K'. To a mixture of compound A' (50 mg, 0.162 mmol) and J (1.1 eqv.) in THF 2 mL was added aqueous solution of 1 M $CuSO_4$ 100 μL and 1 M sodium ascorbate 100 μL. The mixture was stirred at room temperature for 3 h. The reaction mixture was extracted with Ethyl acetate (3×50 mL) and purified by flash chromatography (10% DCM/Methanol). $^1$H NMR (400 MHz, $CD_3Cl$): δ 7.81 (1H, s), 7.80~7.78 (2H, m), 7.55~7.51 (4H, m), 7.02~6.98 (2H, m), 4.60 (1H, t), 4.34 (2H, d), 4.14 (2H, t), 4.11~3.68 (4H, br), 3.49 (2H, s), 2.40 (4H, m), 2.26~2.16 (2H, m) ppm. $^{19}$F NMR (300 MHz, $CD_3Cl$): δ −22.4 (1F, m). HRMS (ESI-TOF) m/z: $[M+H]^+$ Calcd for $C_{23}H_{28}FN_5O_4S$ 490.18; Found 490.19.

In Vitro Affinity Assay.

MDA-MB-231 cells were cultured in an eight-well slide chamber for two days. The cells were pre-incubated with the test compound K for 15 min, and then fixed with 4% formaldehyde. The fixed cells were subsequently incubated for 45 min with biotinylated-TN (CXCR4-specific antagonist peptide). Then, cells were incubated for 30 min in streptavidin-rhodamine at a 1:150 dilution (Jackson Immuno Research Laboratories, West Grove, Pa., USA) after washing three times with PBS. The slides were washed with PBS and mounted in an anti-fade mounting solution (Molecular Probes, Eugene, Oreg., USA). The pictures of stained cells for each treatment were taken on a Nikon Eclipse E800 microscope as follows. Pictures were analyzed quantitatively with ImageJ. The inhibition % of compound K was tested at 0.01, 0.1, 1, 10, 100, 1000, and 10000 nM and $IC_{50}$ value for the compound K was fitted with GraphPad Prism 4. Binding affinity data is shown in FIG. 11.

In Vitro Matrigel Invasion Assay.

Matrigel invasion chambers from BD Biocoat Cellware (San Jose, Calif., USA) were used for invasion assays. MDA-MB-231 cells were cultured on a layer of Matrigel in the upper chamber with DS-219 at 1, 10, 100, and 1000 nM, while 200 ng/ml of CXCL12 was added in the lower chamber as a chemoattractant. The Matrigel invasion chamber was incubated for 22 h in a humidified tissue culture incubator. After noninvading cells were removed from the top of the Matrigel with a cotton-tipped swab. Invading cells at the bottom of the Matrigel were fixed in methanol and stained with H&E. The invasion rate was determined by counting the H&E-stained cells. Data of Matrigel invasion is shown in FIG. 12.

Radiosynthesis.

No-carrier-added $[^{18}F]F^-$ was obtained through the nuclear reaction $^{18}O(p, n)^{18}F$ by irradiation of $^{18}O$-enriched water. After the delivery of $[^{18}F]F^-$ from the cyclotron, the radioactivity was passed through an anion exchange resin cartridge to trap $[^{18}F]F^-$. $[^{18}F]F^-$ was then eluted with a potassium carbonate solution into a vessel containing Kryptofix 2,2,2 ($K_{222}$) and the mixture was dried by azeotropic distillation with acetonitrile. Compound D (or F or H) in anhydrous acetonitrile was added to the dried $K_{222}$/K $[^{18}F]F$ and the mixture was heated at 120° C. for 30 min to produce $[^{18}F]$. The crude reaction mixture was purified by HPLC (Prep column, methanol/water=1/1), then the collected fraction including $[^{18}F]$ compound K was trapped on C18 solid phase extraction cartridge and eluted by ethanol into a vial containing isotonic saline. A total 123 mCi of $[^{18}F]$compound K was obtained from 1389 mCi of $[^{18}F]$-fluoride in a synthesis time of approximately 100 min. The precursor provides a 16.5% decay corrected yield (DCY) of $[^{18}F]$compound K. The saline solution of $[^{18}F]$compound K was sterilized by filtration through a 0.2 micron filter for further study. The cold (radio-inactive) standard compound K was co-injected with dose and HPLC traces displayed the same elution time which supported that the dose was the desired hot compound ($[^{18}F]$ compound K).

In Vitro Competition Binding Assay with [18F]Compound K.

CXCR4-positive metastatic squamous cell carcinoma of head and neck (SCCHN) cells were preincubated with natural ligand CXCL12 (11, 33, and 100 nM) suspension in binding buffer (BB, 1 mg/mL BSA in PBS, 180 μL of cell suspension of 1×107 cells/mL+20 μL of CXCL12 in each tube) for 15 min and 5 μL of [18F]compound K (1 μCi/μL) was added, and then incubated for 60 min with gentle vortexing every 10 min. The tubes were centrifuged and the supernatant was removed, then the cells were washed with 0.5 mL cold BB twice. 200 μL of cold BB was added to each tube and 50 μL of cell suspension was taken from each tube (triplicate). Finally, radioactivity of each tube was measured by a gamma counter. Data for the competitive binding assay is provided in FIG. 13.

In Vivo microPET/CT Study for Inflammation Model with [18F]Compound K.

Acute inflammation was induced by subcutaneous injection of 50 mL of λ-carrageenan (1% w/v in saline) into one of the hind paws of male nude mice (6 weeks, 20 g, Jackson Laboratory, Strain JAZ 007850 J:NU). An apparent edema response was observed 6 days after the λ-carrageenan injection. 150 μCi of radiotracer ($[^{18}F]$compound K) in 150 μL PBS was injected to mice via the tail vein (i.v.). After 50 min, mice were anaesthetized with Isoflurane (1.0~2.0%) and 20 min later (i.e., 70 min after injection of radiotracer), PET images were acquired for 20 min using an Inveon micro PET/CT Preclinical Scanner (Siemens). Subsequent CT images were acquired for 10 min. Paw Edema model displays significant radioactivity in the inflammation. Images are provide in FIG. 14.

In Vivo microPET/CT Study for Head and Neck Cancer Model with [$^{18}$F]Compound K.

SCCHN tumor cells were inoculated (2.5×10$^6$ cells in 50 μL) to female nude mouse (6 weeks, ~20 g, Harlan Sprague Dawley, Strain:HSD:Athymic Nude-Foxn1<nu>) 3 weeks before in vivo test. PET/CT images were acquired using the same protocol as paw edema case. [$^{18}$F]compound K in a head and neck cancer orthotopic primary tumor model reveals significant radioactivity in the tumors. Notably, bone marrow lights up due to enrichment of non-neoplastic CXCR4-positive stem cells. Currently, CXCR4 antagonist AMD3100 is used in clinic for stem cell mobilization. Images are provide in FIG. 15.

In Vivo microPET/CT Study with Cold [$^{19}$F]Compound K (Blocking Study).

A blocking study was performed using cold compound K. Before in vivo assay, toxicity test was performed using cold compound K. 10 mg/kg dose (vehicle: 10% DMSO+90% PBS including 45% cyclodextrin) of compound K was injected to the mouse (female, 6 weeks, 20 g, Jackson Laboratory, JAX000819 B6 Cg-Foxn1 <nu>/J.) via the tail vein (i.v.), which showed no toxicity to the mouse. For the blocking, 200 μL of cold DS-219 solution (30 mg/kg, 10%

DMSO, 90% PBS including 45% cyclodextrin) was administered to the mouse (i.p.) (male, 6 weeks, 20 g, Jackson Laboratory, Strain JAZ 007850 J:NU) 30 min prior to [$^{18}$F]compound K injection (i.v.). PET/CT images were acquired using the same protocol as the previous paw edema case. The results displays specific blocking of bone marrow using cold compound K. Images are provided in FIG. 16.

In Vivo microPET/CT Study for Mouse Lung Metastasis Model with [$^{18}$F]Compound K.

Six-week-old female nude mice (Harlan Sprague Dawley, Strain:HSD:Athymic Nude-Foxn1<nu>) were given injections of 2.0×10$^6$ metastatic subclones of E3 (mouse mammary carcinoma cell line) through the tail vein. After 8 weeks, PET/CT images were acquired using the same protocol as paw edema case. Images are provided in FIG. 17.

The invention claimed is:

1. A compound having formula ID,

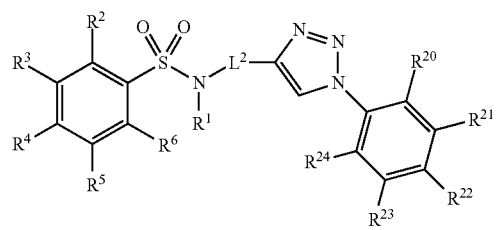

Formula ID or salts thereof, wherein the compound of formula ID comprises a radionuclide selected from the group consisting of $^{11}$C, $^{13}$N, $^{18}$F, $^{76}$Br, $^{123}$I, $^{124}$I, $^{125}$I, and $^{131}$I; and wherein, $R^2$, $R^3$, $R^4$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^2$, $R^3$, $R^4$, $R^5$, and $R^6$, are optionally substituted with one or more, the same or different, $R^{10}$;

$R^{20}$, $R^{21}$, $R^{22}$, $R^{23}$, and $R^{24}$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^{20}$, $R^{21}$, $R^{22}$, $R^{23}$, and $R^{24}$ are a radionuclide or optionally substituted with a radionuclide, or optionally substituted with $R^{30}$, wherein $R^{30}$ is a radionuclide or $R^{30}$ is substituted with a radionuclide;

$L^2$ is a linking group comprising one or more bridging groups selected from —[CH$_2$]—, —[CH$_2$CH$_2$]—, —[CH=CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{30}$ is optionally substituted with one or more, the same or different, $R^{31}$;

$R^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{31}$ is optionally substituted with one or more, the same or different, $R^{32}$; and $R^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein $R^{22}$ is alkoxy terminally substituted with a radionuclide.

3. A compound having formula IF,

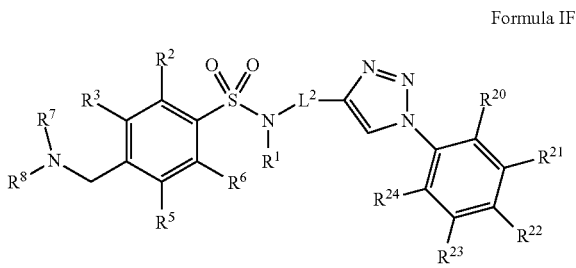

Formula IF or salts thereof wherein, $R^2$, $R^3$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^2$, $R^3$, $R^5$, and $R^6$, are optionally substituted with one or more, the same or different, $R_{10}$;

$R^7$ and $R^8$ form a heterocyclyl optionally substituted with one or more, the same or different, $R^{10}$; or $R^7$ and $R^8$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^7$ and $R^8$, are optionally substituted with one or more, the same or different $R^{10}$;

$R^{20}$, $R^{21}$, $R^{22}$, $R^{23}$, and $R^{24}$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^{20}$, $R^{21}$, $R^{22}$, $R^{23}$, and $R^{24}$ are a radionuclide or optionally substituted with a radionuclide, or optionally substituted with $R_{30}$, wherein $R^{30}$ is a radionuclide or $R^{30}$ is substituted with a radionuclide;

$L^2$ is a linking group comprising one or more bridging groups selected from —[CH$_2$]—, —[CH$_2$CH$_2$]—, —[CH=CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{11}$ is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{30}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{30}$ is optionally substituted with one or more, the same or different, $R^{31}$;

$R^{31}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{31}$ is optionally substituted with one or more, the same or different, $R^{32}$; and $R^{32}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

4. A compound having formula IL,

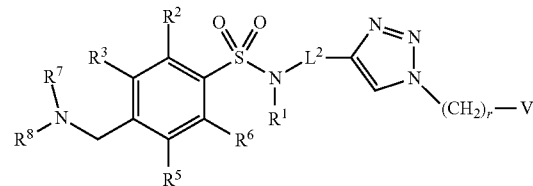

Formula IL or salts thereof wherein, r is 1, 2, 3, 4, 5, 6, 7, or 8;

V is a radionuclide;

$R^2$, $R^3$, $R^5$, and $R^6$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^2$, $R^3$, $R^5$, and $R^6$, are optionally substituted with one or more, the same or different, $R^{10}$;

$R^7$ and $R^8$ form a heterocyclyl optionally substituted with one or more, the same or different, $R^{10}$; or $R^7$ and $R^8$ are each individually and independently hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^7$ and $R^8$, are optionally substituted with one or more, the same or different $R^{10}$;

$L^2$ is a linking group comprising one or more bridging groups selected from —[CH$_2$]—, —[CH$_2$CH$_2$]—, —[CH=CH]—, —O—, —NH—, —S—, —C(O)—, —S(O)—, and —S(O)$_2$—;

$R^1$ is hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkyl sulfonyl, aryl sulfonyl, carbocyclyl, aryl, or heterocyclyl, wherein is optionally substituted with one or more, the same or different, $R^{12}$;

$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

5. A pharmaceutical composition comprising a compound according to claim 1 and a pharmaceutically acceptable excipient.

6. The pharmaceutical composition of claim 5, further comprising another active agent.

7. A method of scanning a subject for radioactivity emissions comprising a) administering compound comprising a radionuclide according to claim 1 to a subject; and b) scanning the subject for radioactivity emissions.

8. The method of claim 7, further comprising the step of detecting the radioactivity emissions and creating an image indicating the location of the compound comprising the radionuclide in the subject.

9. A method of treating rheumatoid arthritis or psoriatic arthritis comprising administering pharmaceutical composition comprising a compound as described in claim 1 to a subject in need thereof.

10. A method of treating an arthritis comprising administering pharmaceutical composition comprising a compound as described in claim 1 in combination with another active ingredient to a subject in need thereof.

11. The method of claim 10, wherein the other active agent is a non-steroidal anti-inflammatory drugs (NSAIDs), ibuprofen, acetaminophen, methotrexate, abatacept, adalimumab, azathioprine, ciclosporin, rituximab, chloroquine, hydroxychloroquine, etanercept, golimumab, infliximab, leflunomide, minocycline, or combinations thereof.

12. A method of treating cancer comprising administering pharmaceutical composition comprising a compound as described in claim 1 to a subject in need thereof.

13. A pharmaceutical composition comprising a compound according to claim 4 and a pharmaceutically acceptable excipient.

14. The pharmaceutical composition of claim 13, further comprising another active agent.

15. A method of scanning a subject for radioactivity emissions comprising a) administering compound comprising a radionuclide according to claim 4 to a subject; and b) scanning the subject for radioactive emissions.

16. The method of claim 15, further comprising the step of detecting the radioactive emissions and creating an image indicating the location of the compound comprising the radionuclide in the subject.

17. A method of treating rheumatoid arthritis or psoriatic arthritis comprising administering pharmaceutical composition comprising a compound as described in claim 4 to a subject in need thereof.

18. A method of treating an arthritis comprising administering pharmaceutical composition comprising a compound as described in claim 4 in combination with another active ingredient to a subject in need thereof.

19. The method of claim 18, wherein the other active agent is a non-steroidal anti-inflammatory drugs (NSAIDs), ibuprofen, acetaminophen, methotrexate, abatacept, adalimumab, azathioprine, ciclosporin, rituximab, chloroquine, hydroxychloroquine, etanercept, golimumab, infliximab, leflunomide, minocycline, or combinations thereof.

20. A method of treating cancer comprising administering pharmaceutical composition comprising a compound as described in claim 4 to a subject in need thereof.

* * * * *